US012226182B2

(12) United States Patent
Swarup

(10) Patent No.: US 12,226,182 B2
(45) Date of Patent: Feb. 18, 2025

(54) BIOLOGICAL MEASUREMENT SYSTEMS AND METHODS

(71) Applicant: Cuica LLC, Plano, TX (US)

(72) Inventor: Ashitosh Swarup, Burbank, CA (US)

(73) Assignee: Cuica LLC, Plano, TX (US)

( * ) Notice: Subject to any disclaimer, the term of this patent is extended or adjusted under 35 U.S.C. 154(b) by 992 days.

(21) Appl. No.: 17/196,672

(22) Filed: Mar. 9, 2021

(65) Prior Publication Data

US 2021/0282690 A1  Sep. 16, 2021

Related U.S. Application Data

(60) Provisional application No. 62/987,686, filed on Mar. 10, 2020.

(51) Int. Cl.
*A61B 5/00* (2006.01)
*A61B 5/0245* (2006.01)
*A61B 5/318* (2021.01)

(52) U.S. Cl.
CPC .......... *A61B 5/0006* (2013.01); *A61B 5/0245* (2013.01); *A61B 5/318* (2021.01); *G06F 2218/04* (2023.01); *G06F 2218/10* (2023.01); *G06F 2218/12* (2023.01)

(58) Field of Classification Search
CPC .......................... A61B 5/0006; G06F 2218/12
See application file for complete search history.

(56) References Cited

U.S. PATENT DOCUMENTS

| | | | | |
|---|---|---|---|---|
| 2008/0304666 | A1* | 12/2008 | Chester | H04J 13/0018 380/263 |
| 2011/0002366 | A1* | 1/2011 | Michaels | H04J 13/0018 375/150 |
| 2017/0373782 | A1* | 12/2017 | Swarup | H04L 27/001 |
| 2018/0199849 | A1* | 7/2018 | Axelrod | A61B 5/08 |
| 2018/0288718 | A1* | 10/2018 | Bal | H04L 7/04 |
| 2020/0107781 | A1* | 4/2020 | Navalgund | A61B 5/0004 |

* cited by examiner

*Primary Examiner* — Fabricio R Murillo Garcia
(74) *Attorney, Agent, or Firm* — David R. Stevens; Stevens Law Group

(57) ABSTRACT

Biological measurement systems and methods are described. In one embodiment, a biological function monitoring system includes a first monitoring device, including a first sensor, a first processor, and a first transmitter. The first sensor senses a first biological function measurement during monitoring a biological function and derives a first data symbol representing the first biological function measurement. The first processor accesses the first data symbol from the first sensor, and combines two or more chaotic waveforms from a first chaotic waveform ensemble, generating a first composite chaotic waveform. The first transmitter transmits the first composite chaotic waveform to a receiver over a communication channel. The biological function monitoring system may include a second monitoring device that is similar to the first monitoring device. The second monitoring device generates a second composite chaotic waveform and transmits the second composite chaotic waveform to the receiver over the communication channel.

20 Claims, 18 Drawing Sheets

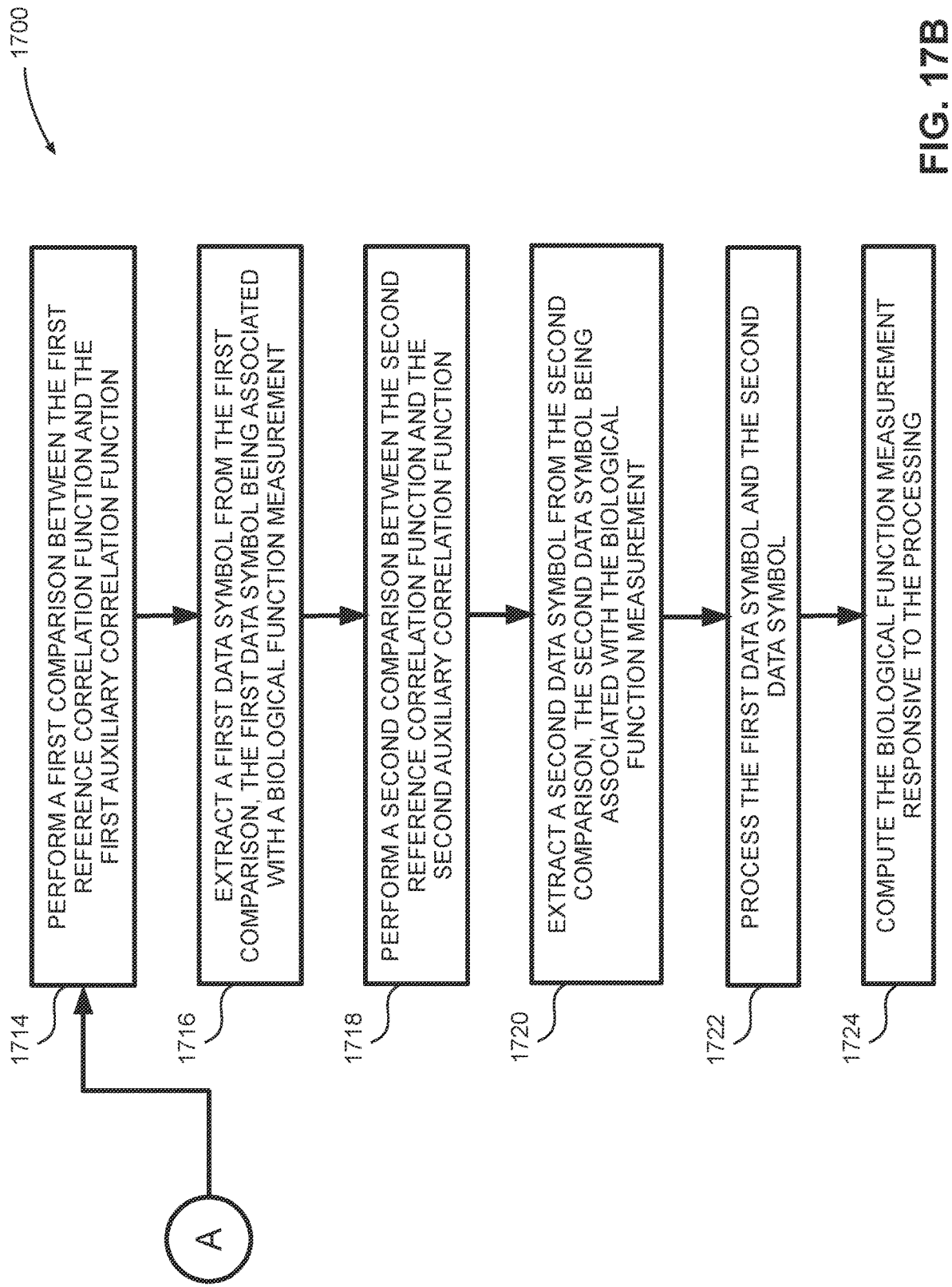

BIOLOGICAL MEASUREMENT SYSTEMS AND METHODS

RELATED APPLICATION

This application claims the priority benefit of U.S. Provisional Application Ser. No. 62/987,686, entitled "Wireless Medical Sensing System Design Using Chaotic Waveforms," filed on Mar. 10, 2020, the disclosure of which is hereby incorporated by reference herein in its entirety.

BACKGROUND

Technical Field

The present disclosure relates to systems and methods that facilitate communication between one or more medical transducers and a receiver using chaotic waveforms.

BACKGROUND ART

Contemporary medical sensing systems such as electrocardiogram (ECG/EKG) systems rely on a wired communication link between each of one or more transducers and an associated back-end processing system. The back-end processing system receives a biological function measurement signal from each transducer via a wired communication link. This back-end processing system processes these biological function measurement signals and computes a biological function measurement such as an ECG/EKG signal. The back-end processing system may display the biological function measurement on a visual display system such as an LCD monitor.

A key drawback of a contemporary ECG/EKG system (and other medical sensing systems) is the wired connectivity required between each transducer and the back-end processing system. An ensemble of wires connecting the transducers is inconvenient to connect/disconnect/reconnect and manage. For example, if a patient has to be moved from one location to another, the transducers have to be disconnected from the back-end processing system and reconnected to another back-end processing system at the destination. Or, the back-end processing system will have to be moved to the destination along with the patient.

SUMMARY

Aspects of the invention are directed to systems and methods to implement a wireless biological measurement system that uses a wireless communication link to communicate data represented in chaotic waveforms and associated with a biological function measurement from a monitoring device (e.g., a transducer and associated processing and transmission circuitry) to a back-end processing system. The communication link can be realized by using one or more chaotic waveform ensembles to implement the link.

A biological function monitoring system that uses chaotic waveforms may include a first monitoring device, including a first sensor, a first processor, and a first transmitter. The first monitoring device may be configured to sense a first biological function measurement (such as an ECG/EKG measurement) during monitoring a biological function, and derive a first data symbol representing the first biological function measurement.

The first processor may be configured to access the first data symbol from the first sensor, and combine two or more chaotic waveforms from a first chaotic waveform ensemble to generate a first composite chaotic waveform representative of the first data symbol. The first transmitter may be configured to transmit the first composite chaotic waveform to a receiver over a communication channel.

The biological function monitoring system may include a second monitoring device, including a second sensor, a second processor, and a second transmitter. The second monitoring device may be configured to sense a second biological function measurement during monitoring the biological function, and derive a second data symbol representing the second biological function measurement.

The second processor may be configured to access the second data symbol from the second sensor, and combine two or more chaotic waveforms from a second chaotic waveform ensemble to generate a second composite chaotic waveform representative of the second data symbol. The second transmitter may be configured to transmit the second composite chaotic waveform to the receiver over the communication channel.

A method to demodulate a combination of received chaotic waveforms may include receiving a first and a second chaotic waveform. The first chaotic waveform may be comprised of at least two distinct chaotic waveforms from a first chaotic waveform ensemble. The first composite chaotic waveform may represent a first data symbol associated with a biological function measurement. The method may include receiving the second composite chaotic waveform. The second composite chaotic waveform may be comprised of at least two distinct chaotic waveforms from a second chaotic waveform ensemble distinct from the first chaotic waveform ensemble. The second composite chaotic waveform may represent a second data symbol associated with the biological function measurement.

A first demodulation may be performed on the at least two distinct chaotic waveforms from the first composite chaotic waveform to derive a first biological signal. A second demodulation may be performed on the at least two distinct chaotic waveforms from the second composite chaotic waveform to derive a second data symbol. The first and second data symbols may be processed to compute the biological function measurement.

A system to demodulate a combination of received chaotic waveforms may include an RF front end configured to wirelessly receive a chaotic signal and downconvert the chaotic signal, a mixed-signal device configured to digitize the downconverted chaotic signal, and a chaotic demodulator. The chaotic demodulator may be configured to extract a first and a second reference chaotic waveform from the digitized chaotic signal by computing a first and a second reference correlation function respectively. The chaotic demodulator may extract a first and a second auxiliary chaotic waveform from the digitized chaotic signal by computing a first and a second auxiliary correlation function respectively.

The chaotic demodulator may be configured to perform a first comparison between the first reference correlation function and the first auxiliary correlation function, and extract a first data symbol from the first comparison, the first data symbol being associated with a biological function measurement. The chaotic demodulator may perform a second comparison between the second reference correlation function and the second auxiliary correlation function and extract a second data symbol from the second comparison, the second data symbol being associated with the biological function measurement. The chaotic demodulator may process the first data symbol and the second data symbol, and compute the biological function measurement responsive to the processing.

BRIEF DESCRIPTION OF THE DRAWINGS

Non-limiting and non-exhaustive embodiments of the present disclosure are described with reference to the following figures, wherein like reference numerals refer to like parts throughout the various figures unless otherwise specified.

FIGS. 17A and 17B are flow diagrams depicting a method to compute a biological function measurement.

DETAILED DESCRIPTION

Figure 1:
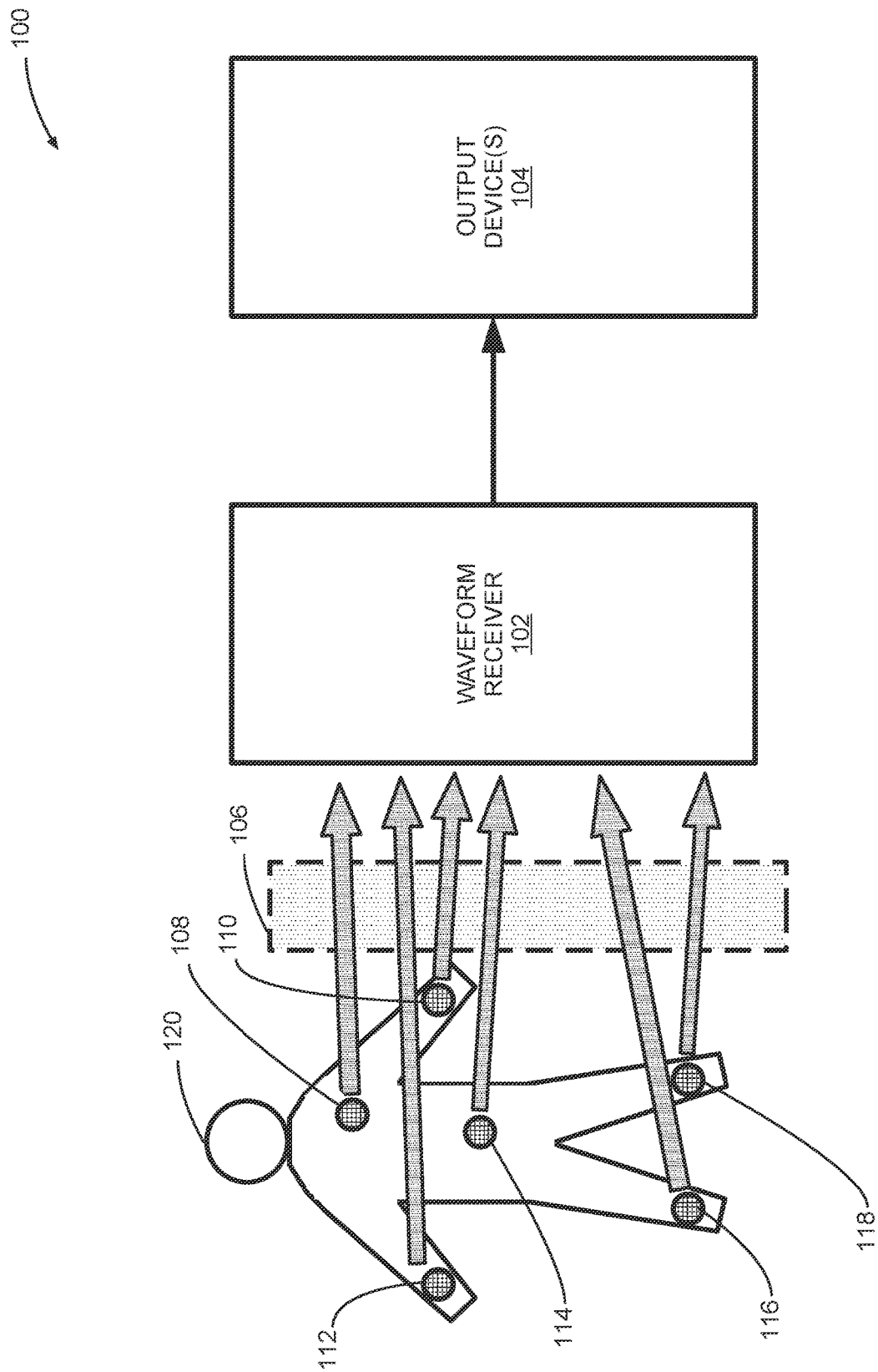
FIG. 1 is a block diagram depicting an example computer architecture of a biological measurement system.

In the following description, reference is made to the accompanying drawings that form a part thereof, and in which is shown by way of illustration specific exemplary embodiments in which the disclosure may be practiced. These embodiments are described in sufficient detail to enable those skilled in the art to practice the concepts disclosed herein, and it is to be understood that modifications to the various disclosed embodiments may be made, and other embodiments may be utilized, without departing from the scope of the present disclosure. The following detailed description is, therefore, not to be taken in a limiting sense.

Reference throughout this specification to "one embodiment," "an embodiment," "one example," or "an example" means that a particular feature, structure, or characteristic described in connection with the embodiment or example is included in at least one embodiment of the present disclosure. Thus, appearances of the phrases "in one embodiment," "in an embodiment," "one example," or "an example" in various places throughout this specification are not necessarily all referring to the same embodiment or example. Furthermore, the particular features, structures, databases, or characteristics may be combined in any suitable combinations and/or sub-combinations in one or more embodiments or examples. In addition, it should be appreciated that the figures provided herewith are for explanation purposes to persons ordinarily skilled in the art and that the drawings are not necessarily drawn to scale.

Embodiments in accordance with the present disclosure may be embodied as an apparatus, method, or computer program product. Accordingly, the present disclosure may take the form of an entirely hardware-comprised embodiment, an entirely software-comprised embodiment (including firmware, resident software, micro-code, etc.), or an embodiment combining software and hardware aspects that may all generally be referred to herein as a "circuit," "module," or "system." Furthermore, embodiments of the present disclosure may take the form of a computer program product embodied in any tangible medium of expression having computer-usable program code embodied in the medium.

Any combination of one or more computer-usable or computer-readable media may be utilized. For example, a computer-readable medium may include one or more of a portable computer diskette, a hard disk, a random-access memory (RAM) device, a read-only memory (ROM) device, an erasable programmable read-only memory (EPROM or Flash memory) device, a portable compact disc read-only memory (CDROM), an optical storage device, a magnetic storage device, and any other storage medium now known or hereafter discovered. Computer program code for carrying out operations of the present disclosure may be written in any combination of one or more programming languages. Such code may be compiled from source code to computer-readable assembly language or machine code suitable for the device or computer on which the code can be executed.

Embodiments may also be implemented in cloud computing environments. In this description and the following claims, "cloud computing" may be defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction and then scaled accordingly. A cloud model can be composed of various characteristics (e.g., on-demand self-service, broad network access, resource pooling, rapid elasticity, and measured service), service models (e.g., Software as a Service ("SaaS"), Platform as a Service ("PaaS"), and Infrastructure as a Service ("IaaS")), and deployment models (e.g., private cloud, community cloud, public cloud, and hybrid cloud).

The flow diagrams and block diagrams in the attached figures illustrate the architecture, functionality, and operation of possible implementations of systems, methods, and computer program products according to various embodiments of the present disclosure. In this regard, each block in the flow diagrams or block diagrams may represent a module, segment, or portion of code, which includes one or more executable instructions for implementing the specified logical function(s). It is also noted that each block of the block diagrams and/or flow diagrams, and combinations of blocks in the block diagrams and/or flow diagrams, may be implemented by special purpose hardware-based systems that perform the specified functions or acts, or combinations of special purpose hardware and computer instructions. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flow diagram and/or block diagram block or blocks.

Aspects of the invention described herein describe systems and methods that implement wireless biological measurement systems using chaotic waveforms.

Chaotic signals can be described as "deterministic noise", which is to say that these signals resemble noise signals in the time and frequency domains, but are generated by nonlinear deterministic systems. These nonlinear systems are very sensitive to initial conditions, with very different temporal waveforms being produced with slight changes in initial conditions. Furthermore, each chaotic system can produce a very large ensemble of uncorrelated chaotic waveforms. These can be generated either using analog flows, such as the Chua Double Scroll Attractor, or discrete-time chaotic maps. Analog circuitry generates analog chaotic signals that are solutions to nonlinear differential equations, whereas discrete-time nonlinear state equations generate discrete-time chaotic sequences. Two examples of discrete-time chaotic function generators are:

$$x_{k+1} = 1 - 2x_k^2 \quad \text{Logistic map:}$$

$$x_{k+1} = 4x_k^3 - 3k_k \quad \text{Cubic map:}$$

Some of the properties of chaotic waveforms are:

Chaotic waveforms are generated by nonlinear dynamic systems, in the continuous-time domain (via nonlinear differential equations) and in the discrete-time domain (via nonlinear discrete-time recursions—difference equations).

Chaotic waveforms resemble noise in the time- and frequency domains, but are deterministic in nature.

Chaotic systems are very sensitive to initial conditions—even a slight change in initial conditions produces a waveform that is uncorrelated with the original waveform. On the other hand, for a given chaotic system and initial condition, a chaotic waveform is repeatable.

Continuous-time chaotic waveforms are aperiodic—chaotic waveforms of arbitrarily long lengths can be generated.

Discrete-time chaotic waveforms are substantially aperiodic for substantially infinite numerical precision (i.e., analog value) per sample; reducing the numerical precision (e.g. limited-width fixed-point numerical representation) results in periodic orbits.

Chaotic waveform ensembles show strong autocorrelations and weak cross-correlations, a property referred to as quasi-orthogonality.

Chaotic signals are inherently wideband, and therefore are good candidate waveforms for spread-spectrum communication systems. The wideband nature of these signals also makes them resistant to noise and interference from other signals.

A large ensemble of quasi-orthogonal waveforms can be generated for each cubic map, a property referred to as waveform diversity.

A large number of chaotic waveforms can be transmitted simultaneously with minimal inter-waveform interference—this is the code-division multiple access (CDMA) property associated with spread-spectrum communication systems.

A result of these properties is that the number of degrees of freedom for the system designer now increases—rather than being limited by waveform and temporal length constraints, the system designer is now able to construct a relatively large quasi-orthogonal waveform ensemble of any arbitrary length (subject to numerical precision constraints). When used in a communication system, a chaotic signal provides a layer of security at the waveform level, in the sense that only a party with a priori knowledge of the chaotic waveform ensemble and a corresponding codebook can decipher the information being transmitted using the chaotic waveform ensemble. This property is especially useful in designing secure waveform families—in addition to digital data encryption, chaotic waveforms offer an additional layer of security at the waveform level.

An additional advantage of chaotic signals, a class of spread-spectrum signals, is their anti-jam capability as well as their ability to operate below the noise floor. It is not possible to determine, in general, any characteristics of the underlying signal using conventional spectral analysis techniques such as a spectroscope or a frequency analyzer.

For designing medical sensing systems using chaotic waveforms, one goal is to replace a wired connection between a transducer and a computing system or processing system by a chaotic communication link. In order to do so, the following properties of chaotic waveforms may be used:

Quasi-orthogonality: The strong autocorrelation and low cross-correlation properties of chaotic waveforms enable multiple waveforms to be transmitted simultaneously and demodulated without ambiguity at the receiver. In this way, multiple wireless-enabled transducers (or monitoring devices) function simultaneously on a patient, and parallel channels of chaotically-modulated data can be unambiguously streamed wirelessly to a digital processing back end. Assuming a unique set of chaotic waveforms associated with each monitoring device, a monitoring device may be identified based on a received waveform ensemble. This property resolves any node identification ambiguity.

Operation with power levels below the noise floor: With suitable system design, chaotic waveforms can be transmitted below the noise floor, thereby requiring reduce transmit power. Furthermore, transmitting signals at a lower power level reduces any disturbance from these waveforms to other wireless systems.

Robust performance: Chaotic waveforms also possess excellent anti jam properties that enable these waveforms to be functional even in the presence of external interference.

Novel chaotic modulation schemes for increased spectral efficiency: Chaotic waveform modulation schemes allow for low-power, high data rate communication links to be established and maintained.

FIG. 1 is a block diagram depicting an example computer architecture of a biological measurement system 100. As depicted, biological measurement system 100 (also referred to as a "biological function monitoring system") includes a plurality of monitoring devices—a monitoring device 108, a monitoring device 110, a monitoring device 112, a monitoring device 114, a monitoring device 116, and a monitoring device 118 attached to a biological entity 120. In an aspect, biological entity 120 may be a human being or an animal (e.g., a dog). Each of monitoring device 108 through monitoring device 118 may include a biomedical transducer such as an ECG/EKG transducer.

In an aspect, each of monitoring device 108 through monitoring device 118 may be configured to measure one or more biological function measurements. For example, biological entity 120 may be a human being, and each of monitoring device 108 through monitoring device 118 may be associated with an ECG/EKG measurement. In an aspect, each of monitoring device 108 through monitoring device 118 is configured to modulate a data symbol associated with the respective biological function measurement onto multiple, distinct chaotic waveforms from a chaotic waveform ensemble, to generate a composite chaotic waveform. Each of monitoring device 108 through monitoring device 118 may be configured to transmit the associated composite chaotic waveform over a communication channel 106, to a waveform receiver 102. In an aspect, communication channel 106 may be a wireless communication channel. In an aspect, each of monitoring device 108 through monitoring device 118 may store a distinct chaotic waveform ensemble, where each chaotic waveform ensemble associated with a monitoring device is a unique set of chaotic waveforms that is distinct from all other chaotic waveform ensembles associate with the other monitoring devices.

Waveform receiver 102 may be configured to receive a composite chaotic waveform from each of monitoring device 108 through monitoring device 118, demodulate the composite chaotic waveform, and extract a data symbol associated with the biological function measurement. Waveform receiver 102 may further process each data symbol to compute the biological function measurement.

The biological function measurement computed by receiver 102 may be transmitted to one or more output device(s) 104 for display to a user of biological measurement system 100. Examples of output device(s) 104 include visual display monitors (e.g., LCD, LED, or CRT displays), graphical plotting devices, audio devices such as loudspeakers, and other visual display devices such as LED lamps or bulbs.

An example application of biological measurement system 100 is an ECG/EKG measurement system, where each of monitoring device 108 through monitoring device 118 may include an ECG/EKG transducer. Each ECG/EKG transducer in each monitoring device may be configured to measure an ECG/EKG biological signal at an appropriate part of the human body, digitize the ECG/EKG biological signal, modulate the digitized ECG/EKG biological signal by combining multiple chaotic waveforms, and transmit the modulated chaotic waveforms to waveform receiver 102. Waveform receiver 102 demodulates the received modulated chaotic waveforms by performing operations such as one or more correlations, and extracts one or more data symbols from each demodulation (e.g., correlation) process. In an aspect, each data symbol corresponds to an ECG/EKG transducer measurement, and may be similar to a measurement gathered by a contemporary wired ECG/EKG device. Waveform receiver 102 may analyze the data symbols, and generate an ECG/EKG signal based on the data symbols. This ECG/EKG signal may be displayed to a user on output devices 104.

Figure 2:
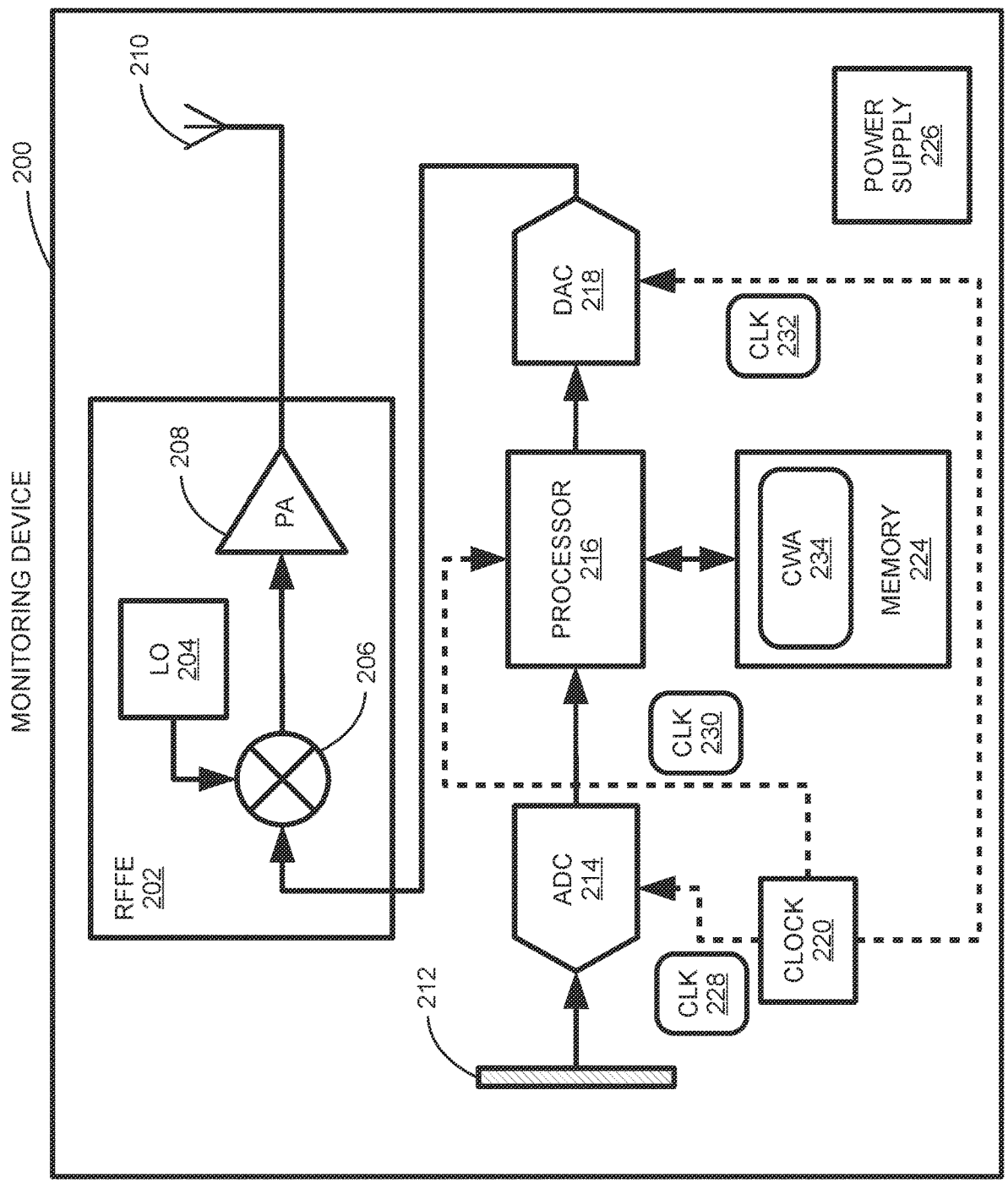
FIG. 2 is a block diagram depicting an example computer architecture of a monitoring device.

Other applications where the chaotic waveform-based modulation scheme may be used to implement wireless biological measurement systems include:
Cardiology
    Pulse oximetry
    Blood pressure (arterial, venous)
    Neuromodulation during spine surgery
    Temperature
    Echocardiography
    Post-op intensive care unit recording
    Pacemaker function diagnosis
Neurology
    Electroencephalogram
    Tumor diagnosis
    Brain clot (trauma) detection FIG. 2 is a block diagram depicting an example computer architecture of a monitoring device 200. The architecture of monitoring device 200 may be used to implement any, some, or all of monitoring device 108 through monitoring device 118. As depicted, monitoring device 200 includes a sensor 212, a clock 220, an analog-to-digital converter ADC 214, a processor 216, a memory 224, a digital-to-analog converter DAC 218, an RF front end RFFE 202, a transmit antenna 210, and a power supply 226. RFFE 202 may further include an upconverting mixer 206, a local oscillator LO 204, and a power amplifier PA 208. In an aspect, processor 216 may be implemented on a suitable processing device such as a field-programmable gate array (FPGA), a microcontroller, a digital signal processor (DSP), or a customized integrated circuit.

In an aspect, sensor 212 may be a biomedical transducer such as an ECG/EKG transducer, or some other transducer configured to measure a biological signal. Sensor 212 may be configured to measure (i.e., sense) a biological function measurement during monitoring a biological function (e.g., heart rate). Sensor 212 may output an analog signal based on the biological function measurement. This analog signal may be digitized by ADC 214 to generate a digital data symbol (i.e., a digital data sample) corresponding to the biological function measurement. The digital data symbol may be input to processor 216.

In an aspect, memory 224 may be configured to store an ensemble of (i.e., two or more) chaotic waveforms of a given temporal length, such as, for example, chaotic waveform ensemble (CWA) 234. These chaotic waveforms may be written to memory 224 from an external source, or may be generated by processor 216 and written to memory 224. In an aspect, the chaotic waveforms stored in memory 224 may be discrete-time, digitized chaotic waveforms generated in the digital domain using nonlinear recursions.

In an aspect, processor 216 may be configured to read (e.g., two or more) chaotic waveforms from a chaotic waveform ensemble, for example, CWA 234, stored in memory 224, and combine the chaotic waveforms based on the digital data symbol read from ADC 214, to generate a composite chaotic waveform. This process is a chaotic modulation process, where two or more chaotic waveforms are modulated in accordance with the digital data symbol.

In an aspect, processor 216 outputs the composite chaotic waveform (a digital waveform modulated with the digital data symbol) to DAC 218. DAC 218 converts the (digital) composite chaotic waveform into an analog waveform. In an aspect, ADC 214, processor 216, and DAC 218 function using one or more clock signals generated by clock 220. For example, clock 220 may generate clock signals CLK 228 input to ADC 214, CLK 230 input to processor 216, and CLK 232 input to DAC 218.

The analog waveform generated by DAC 218 is input to upconverting mixer 206, where the analog waveform is mixed with a sinusoidal signal from LO 204, and upconverted to a waveform at a frequency suitable for transmission over communication channel 106. PA 208 receives the upconverted signal and amplifies the power of the signal, and then transmits the amplified signal to transmit antenna 210 for wireless transmission over communication channel 106.

In an aspect, the different components of monitoring device 226 may be powered by electrical power generated by power supply 226. Power supply 226 may be a disposable or rechargeable battery, or a power harvesting circuit that may derive electrical power from, for example, heat generated by biological entity 120. The mixed-signal blocks associated with monitoring device 200 (i.e., ADC 214 and DAC 218) may include additional amplification and filtering components as required for appropriate signal conditioning.

In an aspect, monitoring device 200 may be integrated and packaged into an appropriate format and form factor appropriate to the desired application (e.g., an adhesive transducer to be applied to a patient's skin, or an oxygen sensor attached to a patient's finger).

Figure 3:
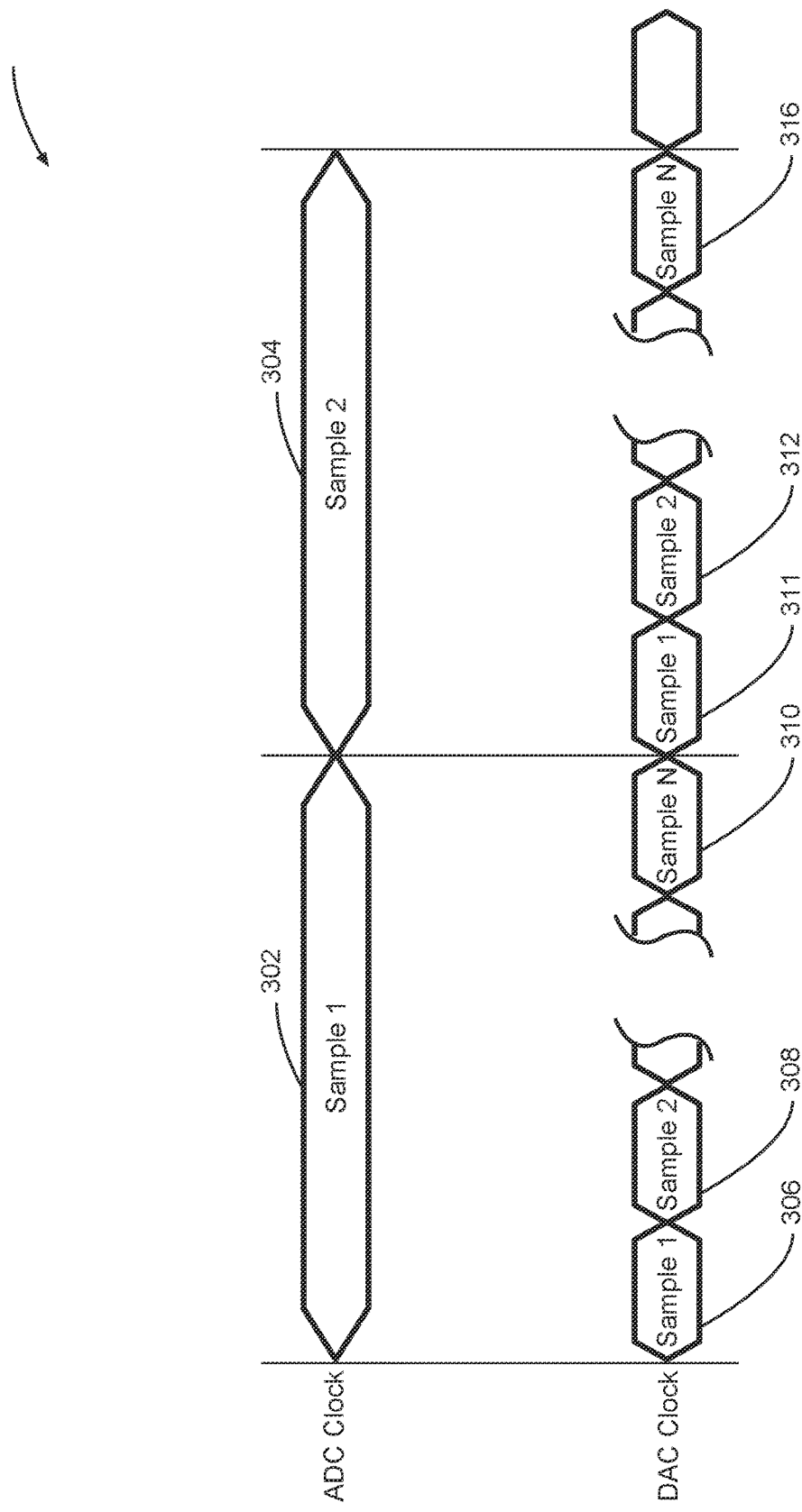
FIG. 3 is a timing diagram depicting a relationship between an ADC clock and a DAC clock.

FIG. 3 is a timing diagram depicting a relationship 300 between an ADC clock and a DAC clock. Chaotic waveforms are spread-spectrum waveforms; each data sample measured by sensor 212 and digitized by ADC 214 modulates a chaotic waveform that is N samples long, where N>1. Examples of N include lengths of 100 samples, 200 samples, 512 samples, 1024 samples, and so on, of chaotic waveform lengths. Relationship 300 shows a sample 1 302 and a sample 2 304 generated by sensor 212 at a rate associated with an ADC clock (e.g., CLK 228). Each of sample 1 302 and sample 2 304 is mapped to a composite chaotic waveform, as indicated in relationship 300. For a composite chaotic waveform that is N samples long, CLK 232 associated with DAC 218 may be a clock that has a frequency that is N-times that of CLK 228. This DAC clock (e.g., CLK 232) may be generated or derived from CLK 228 using, for example a clock multiplier.

Relationship 300 shows sample 1 302 being chaotically modulated to generate a composite chaotic waveform comprising a sample 1 306, a sample 2 308, through a sample N 310, clocked at a rate corresponding to the DAC clock frequency. Similarly, sample 2 304 is chaotically modulated to generate a composite chaotic waveform comprising a sample 1 312, a sample 2 314, through a sample N 316, clocked at a rate corresponding to the DAC clock frequency.

Figure 4:
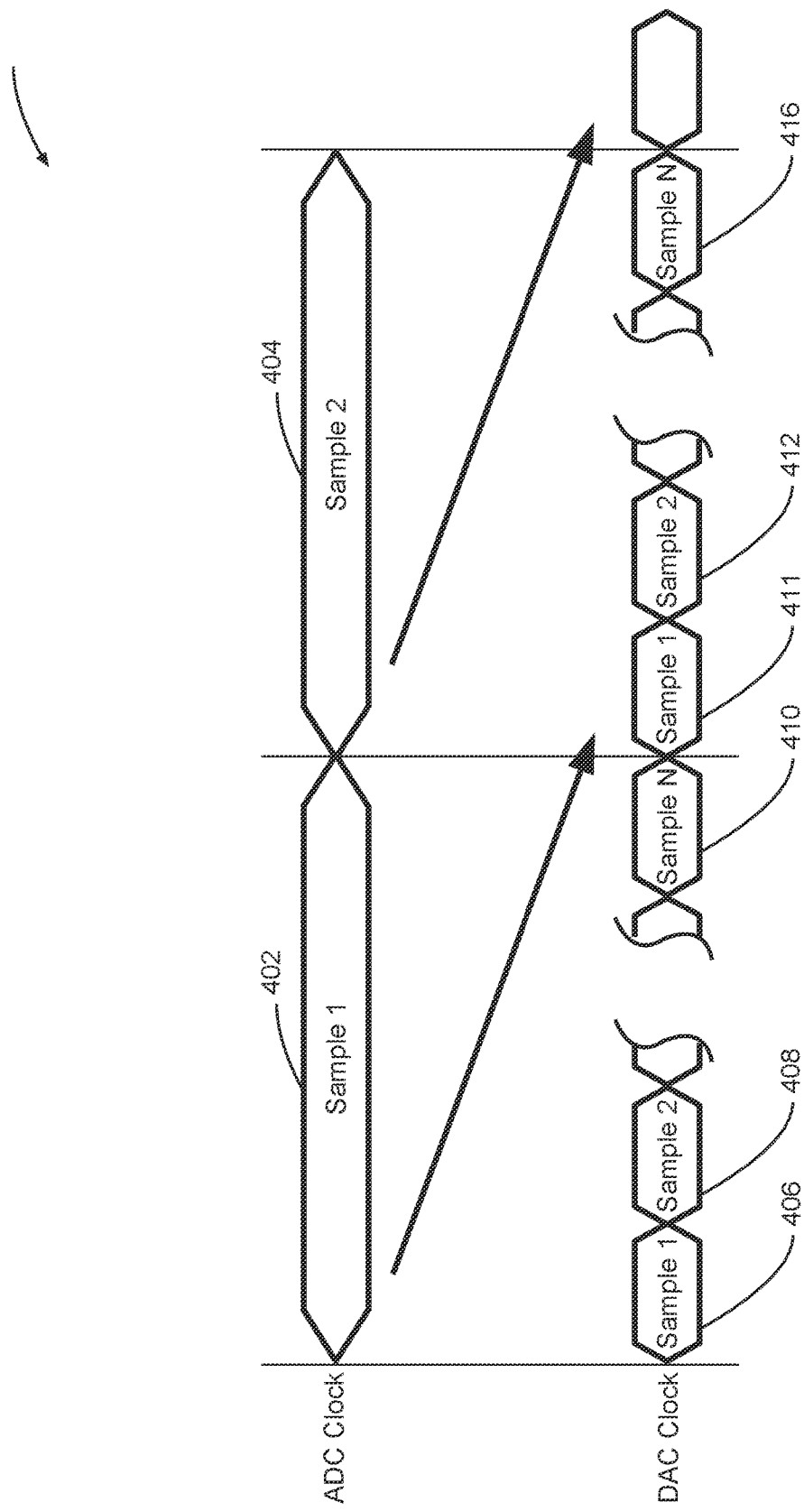
FIG. 4 is a timing diagram depicting a one-sample delay.

FIG. 4 is a timing diagram depicting a one-sample delay 400. Relationship 300 depicts an ideal (theoretical) relationship between an ADC clock and a DAC clock. The representation of relationship 300 assumes that digitized data is available at the output of ADC instantaneously. In a practical system, every ADC is associated with a finite conversion time; hence, there is some latency between an analog input to ADC 214, and a digitized output from ADC 214. One-sample delay 400 represents this latency, where a sample 1 402 read at the ADC clock frequency is mapped to a sample 1 411, a sample 2 412, through a sample N 414 of a composite chaotic sequence.

A digitized data sample generated before sample 1 402 (not shown in FIG. 4) is mapped to samples of an earlier composite chaotic sequence, i.e., a sample 1 406, a sample 2 408, through a sample N 410. A sample 2 404 that is subsequent to sample 1 402 is mapped to a composite chaotic waveform subsequent to the composite chaotic waveform (not shown in FIG. 4) that sample 1 402 is mapped to. During the mapping process, processor 216 may be in the process of reading in a subsequent digitized data sample from ADC 214. In general, a composite chaotic sequence corresponding to an $n^{th}$ data sample is output when the $(n+1)^{th}$ data sample is being read in by processor 216.

Figure 5:
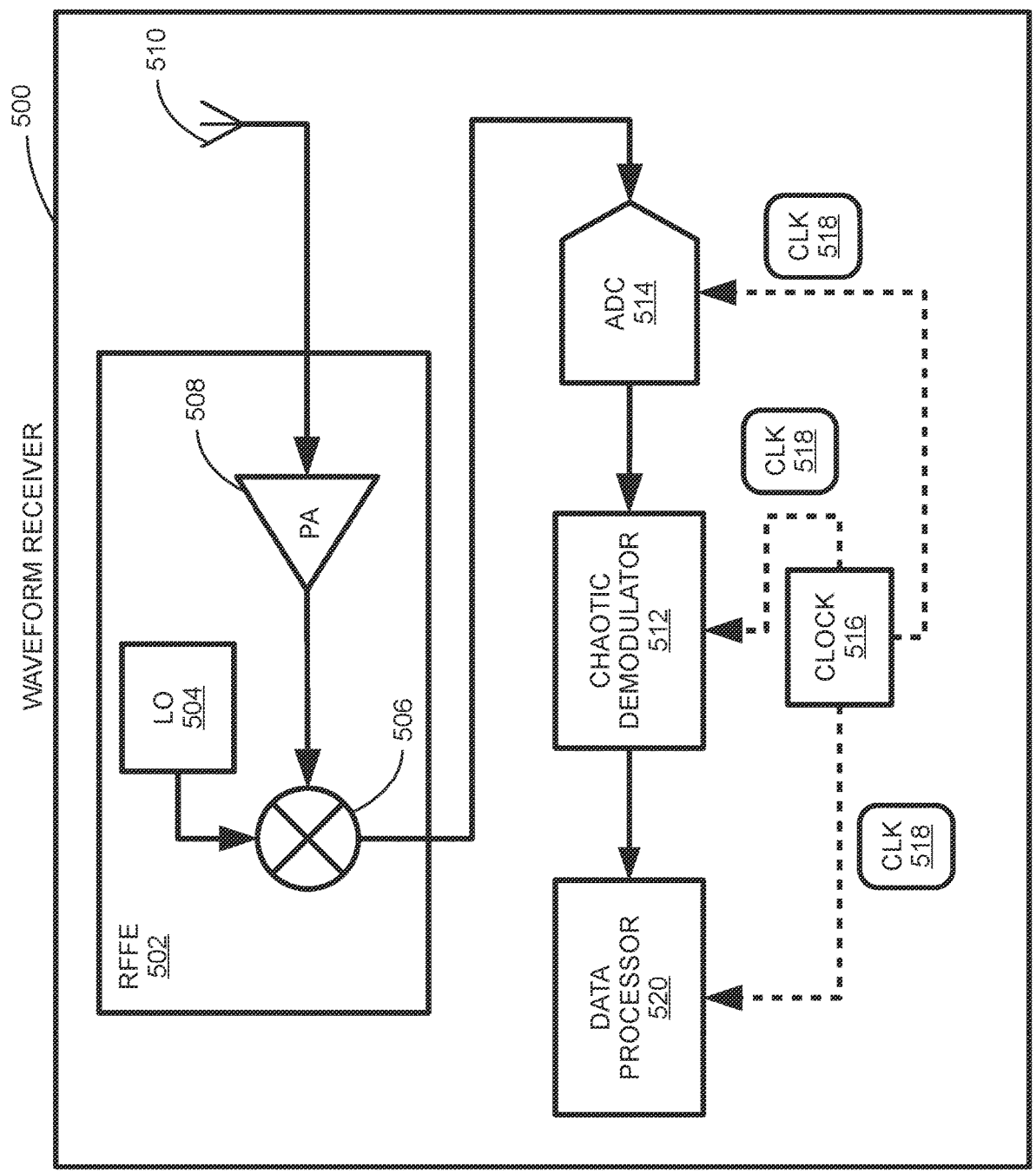
FIG. 5 is a block diagram depicting an example computer architecture of a waveform receiver.

FIG. 5 is a block diagram depicting an example computer architecture of a waveform receiver 500. Waveform receiver 500 may be configured to receive and demodulate one or more composite chaotic waveforms generated by one or more monitoring devices such as monitoring device 108 through monitoring device 118. In an aspect, waveform receiver 500 may be identical to waveform receiver 102.

As depicted, waveform receiver 500 may include a receive antenna 510, an RF front end RFFE 502, an analog-to-digital converter ADC 514, a chaotic demodulator 512, a clock 516, and a data processor 520. RFFE 502 may further include a power amplifier PA 508, a local oscillator LO 504, and a downconverting mixer 506.

In an aspect, receive antenna 510 may be configured to receive one or more composite chaotic waveforms over communication channel 106 from each of monitoring device 108 through monitoring device 118. PA 508 may appropriately amplify and filter the received composite chaotic waveforms, which are downconverted to a suitable intermediate frequency (IF) by downconverting mixer 506. Downconverting mixer 506 may use a locally generated sinusoidal function generated by LO 504 to accomplish the downconversion process.

In an aspect, the downconverted signal at an intermediate frequency (IF) is received from the output of the downconverting mixer by ADC 514. ADC 514 digitizes the received analog signal and outputs the digitized signal to chaotic demodulator 512. Chaotic demodulator 512 may demodulate the received digitized composite chaotic waveforms and extract one or more data symbols from demodulating each digitized composite chaotic waveform. In an aspect, a demodulation process may be implemented as a correlation with locally-stored replica copies of the chaotic waveforms. All data symbols extracted from the demodulation processes are output by chaotic demodulator 512 to data processor 520. Data processor 520 may be configured to collectively processes all received data symbols and compute a biological function measurement. This biological function measurement may be, for example, an ECG/EKG measurement as measured by monitoring device 108 through monitoring device 118. In an aspect, data processor 520 and all functions of data processor 520 may be integrated into chaotic demodulator 512.

In an aspect, clock 516 provides a clock signal CLK 518 that is routed to ADC 514, chaotic demodulator 512, and data processor 520 for maintaining timing and synchronization.

Figure 6:
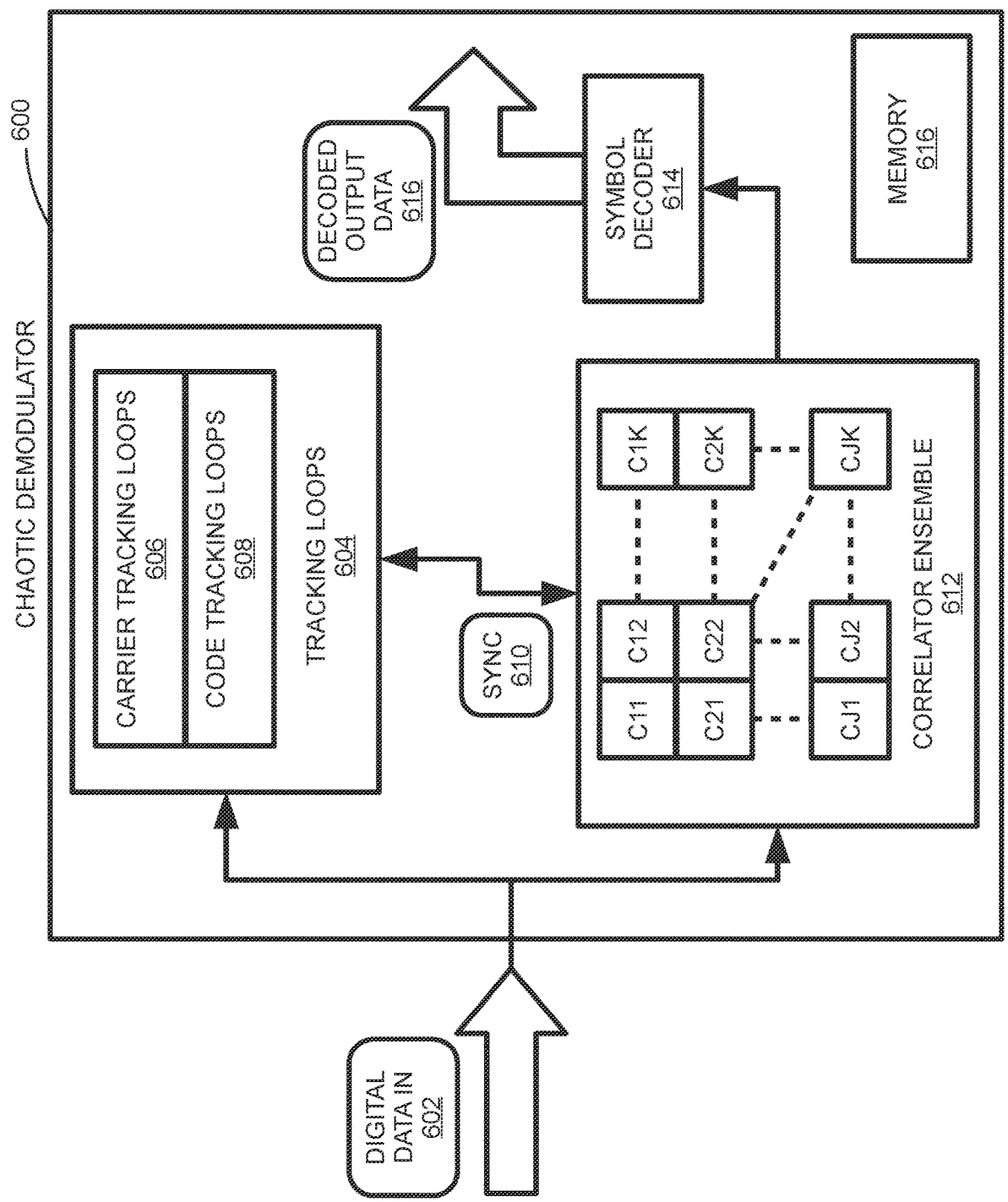
FIG. 6 is a block diagram depicting an example computer architecture of a chaotic demodulator.

FIG. 6 is a block diagram depicting an example computer architecture of a chaotic demodulator 600. In an aspect, chaotic demodulator 600 may be similar to chaotic demodulator 512. As depicted, chaotic demodulator 600 may include tracking loops 604, a correlator ensemble 612, a symbol decoder 614, and a memory 616. Tracking loops 604 may further include carrier tracking loops 606 and code tracking loops 608. Correlator ensemble 612 may be further comprised of a plurality of correlators—C11, C12 through C1K, C21, C22 through C2K, and CJ1, CJ2 through CJK. Correlators C11 through CJK may be configured as a correlator array. In an aspect, chaotic demodulator 600 may be implemented on a suitable processing device such as a field-programmable gate array (FPGA), a microcontroller, a digital signal processor (DSP), a personal computer, a customized integrated circuit-based processing system, or any other suitable processing device.

In an aspect, chaotic demodulator 600 receives digital data in 602. Digital data in 602 may be digitized data received from ADC 514. Digital data 602 may be routed to tracking loops 604 and to correlator ensemble 612. Tracking loops 604 comprising carrier tracking loops 606 and code tracking loops 608 perform carrier tracking and code tracking functions, respectively, on one or more chaotic waveforms received from each of monitoring device 108 through 118 as digital data in 602. Carrier tracking loops 606 and code tracking loops 608 track and maintain a lock on timing and synchronization on any received composite chaotic waveform. Carrier tracking loops 606 function by comparing a sinusoidal carrier signal associated with each received composite chaotic waveform and a locally-generated or locally-stored sinusoidal signal. Code tracking loops 608 function by comparing a digitized composite chaotic waveform and one or more locally-generated or locally-stored chaotic waveforms. In an aspect, the locally-generated/locally-stored sinusoidal signal and chaotic waveforms may be stored in memory 616, and retrieved by carrier tracking loops 606 and code tracking loops 608 as necessary. In an aspect carrier tracking loops 606 may include one or more phase-locked loops (PLLs), while code tracking loops 608 may include one or more delay-locked loops (DLLs).

In an aspect, each of C11 through CJK within correlator ensemble 612 may be configured to perform a correlation operation associated with a distinct chaotic waveform. Each composite chaotic waveform received by chaotic demodulator 600 may be correlated against a distinct locally-generated/locally-stored chaotic waveform replica, in each of C11 through CJK. In an aspect, the correlations are performed using a parallel-processing approach. In one aspect, each of C11 through CJK may be dedicated to performing a single correlation operation. In another aspect, each of C11 through CJK may perform multiple correlation operations. Each locally-generated/locally-stored chaotic waveform replica may be stored in memory 616.

In an aspect, one or more synchronization signals SYNC 610 may be used to maintain timing and synchronization between tracking loops 604 and correlator ensemble 612. Each of C11 through CJK is configured to perform one or more correlations and output the results of the correlations to symbol decoder 614. Symbol decoder 614 may be configured to derive a data symbol from each of the correlation results. The data symbols derived by symbol decoder 614 may be output as decoded output data 616. This decoded output data 616 may be further processed by data processor 520 to compute a biological function measurement (e.g., an ECG/EKG measurement).

In an aspect, correlator ensemble 612 may be implemented using multi-core processing platforms such as multi-correlator-configured FPGAs, multi-core processing architectures, GPU arrays, or other massively-parallel computing architectures.

Figure 7:
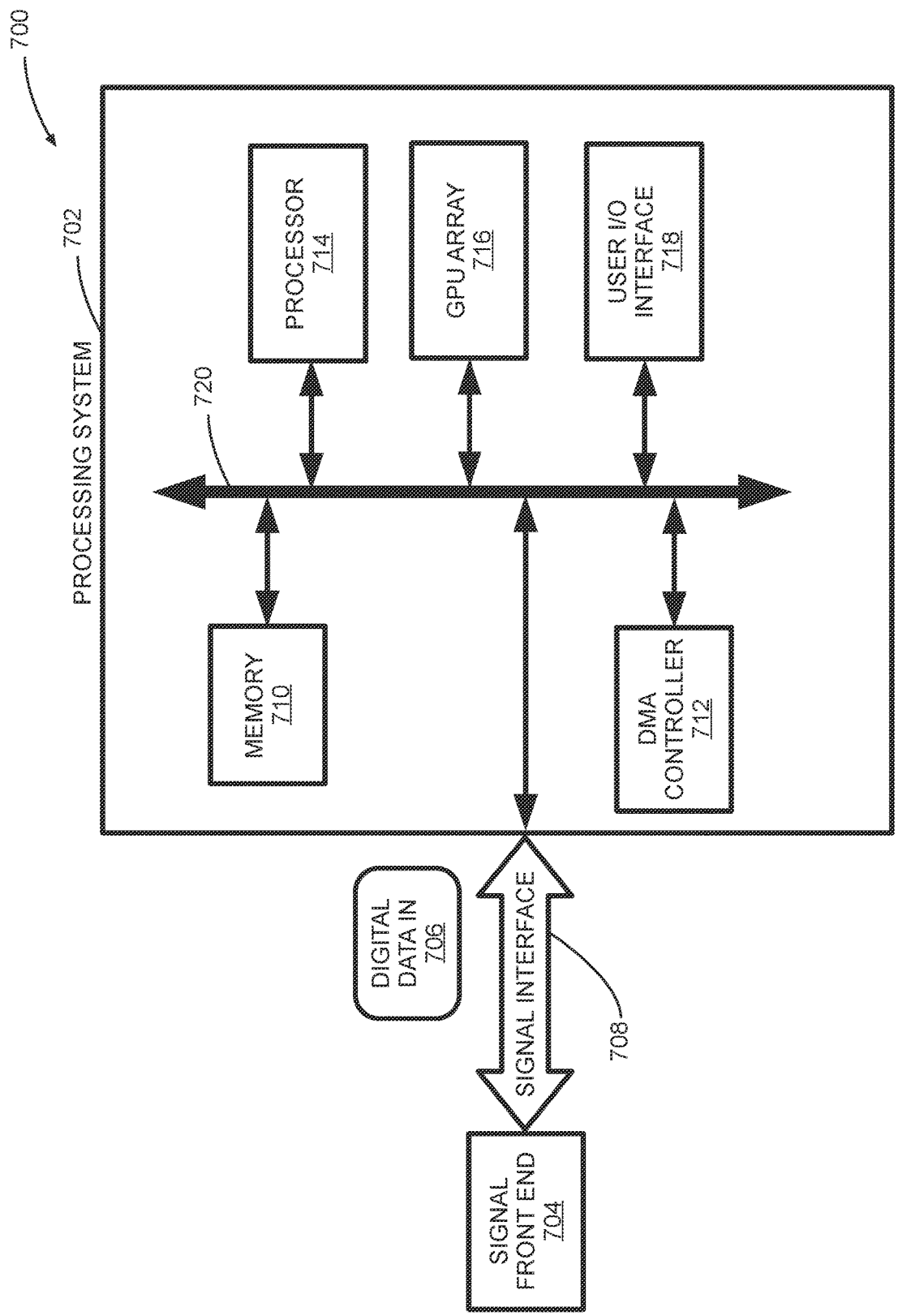
FIG. 7 is a block diagram depicting an example computer architecture of a waveform receiver.

FIG. 7 is a block diagram depicting an example computer architecture of a waveform receiver 700. Waveform receiver 700 may perform functions similar to waveform receiver 102. As depicted, waveform receiver 700 may include a signal front end 704, a signal interface 708, and a processing system 702. Processing system 702 may further include a memory 710, a DMA controller 712, a processor 714, a GPU array 716, and a user I/O interface 718. A data bus 720 may communicatively couple the components of processing system 702.

In an aspect, signal front end 704 may be configured to perform functions of receive antenna 510, RFFE 502, and ADC 514. Signal front end 704 may be configured to wirelessly receive one or more composite chaotic waveforms from monitoring device 108 through monitoring device 118, downconvert the composite chaotic waveforms, and digitize the downconverted composite chaotic waveforms to generate a digitized signal. The digitized signal may be communicated to processing system 702 via signal interface 708 as digital data in 706. Signal interface 708 may also support exchange of timing, handshaking and other signals between signal front end 704 and processing system 702. Examples of signal interface 708 include USB, serial interface(s), serial port(s), parallel ports, LVDS signaling interface(s), and so on. In an aspect, signal front end 704 may be designed and configured in the form of a USB dongle.

In an aspect, processing system 702 may be configured to receive the downconverted composite chaotic waveforms, and perform functions similar to chaotic demodulator 512 and data processor 520. In an aspect, GPU array 716 may be used to implement functions of correlator ensemble 612. Processor 714 may be configured to implement tracking loops 604, symbol decoder 614, and data processor 520. Some correlation operations associated with correlator ensemble 612 may be implemented on processor 714 if processor 714 is a multi-core processor. Some embodiments of processing system 702 may not include GPU array 716, and may instead implement functionalities associated with correlator ensemble 612 on processor 714.

In an aspect, memory 710 may be configured to store local replica copies of chaotic waveforms and sinusoidal carrier waveforms, in a manner similar to memory 616. Memory 710 may also be configured to store digital data in 706. DMA controller 712 may be configured to coordinate data transfer between various components of processing system 702 without intervention of processor 714, over data bus 720.

In an aspect, user I/O interface 718 may be used to interface processing system 702 (and waveform receiver 700) with output device(s) 104. Examples of protocols supported by user I/O interface may include DVI, HDMI, mouse/keyboard interfaces, and so on.

Figure 8:
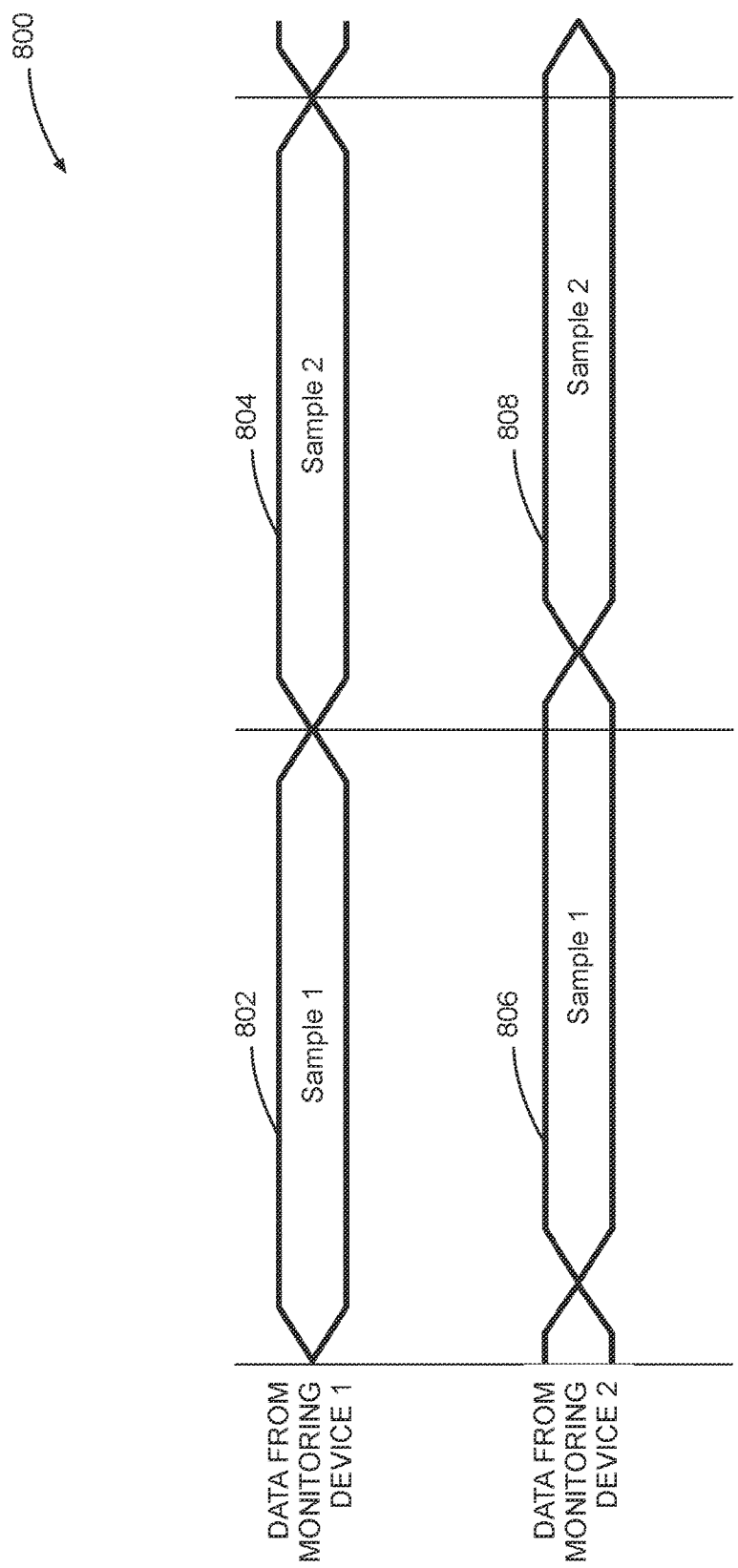
FIG. 8 is a timing diagram depicting an effect of clock non-synchronization.

FIG. 8 is a timing diagram depicting an effect 800 of clock non-synchronization. In an aspect, each of monitoring device 108 through monitoring device 118 may have an independent clock source (e.g., clock 220 associated with monitoring device 200). In an aspect, all monitoring devices associated with biological measurement system 100 may be configured with clock sources that share identical characteristics (e.g., frequency, jitter, etc.). However, due to manufacturing tolerances, the characteristics of the clock sources (e.g., frequency) might not be exactly equal. Such phenomena have important ramifications that need to be taken account during system design.

One clock-related phenomenon that may need to be considered during system design is clock synchronization. For example, consider a first and a second monitoring device that are configured to capture a biological function measurement. The clock signals generated by the respective clock sources may not be synchronized. This effect is depicted as effect 800.

Effect 800 depicts a sample 1 802 and a sample 2 804 from a monitoring device 1 (e.g., monitoring device 108), and a sample 1 806 and a sample 2 808 from a monitoring device 2 (e.g., monitoring device 110). These data samples may be data samples similar to data samples output by ADC 214. Assuming that the clock signals of monitoring device 1 and monitoring device 2 are not aligned, data sample 1 802 will not be aligned with data sample 1 806, data sample 2 804 will not be aligned with data sample 2 808, and so on. For example, using the timing of monitoring device 1 as a reference, if data sample 1 802 is read at t=0 and if the two clock signals are apart by 1 microsecond, data sample 1 806 is read at t=1 microsecond. Due to this reason, the measurements of the biological function from monitoring device 1 and monitoring device 2 are non-synchronous. This may lead to errors when the biological function measurement is computed by waveform receiver 102.

Figure 9:
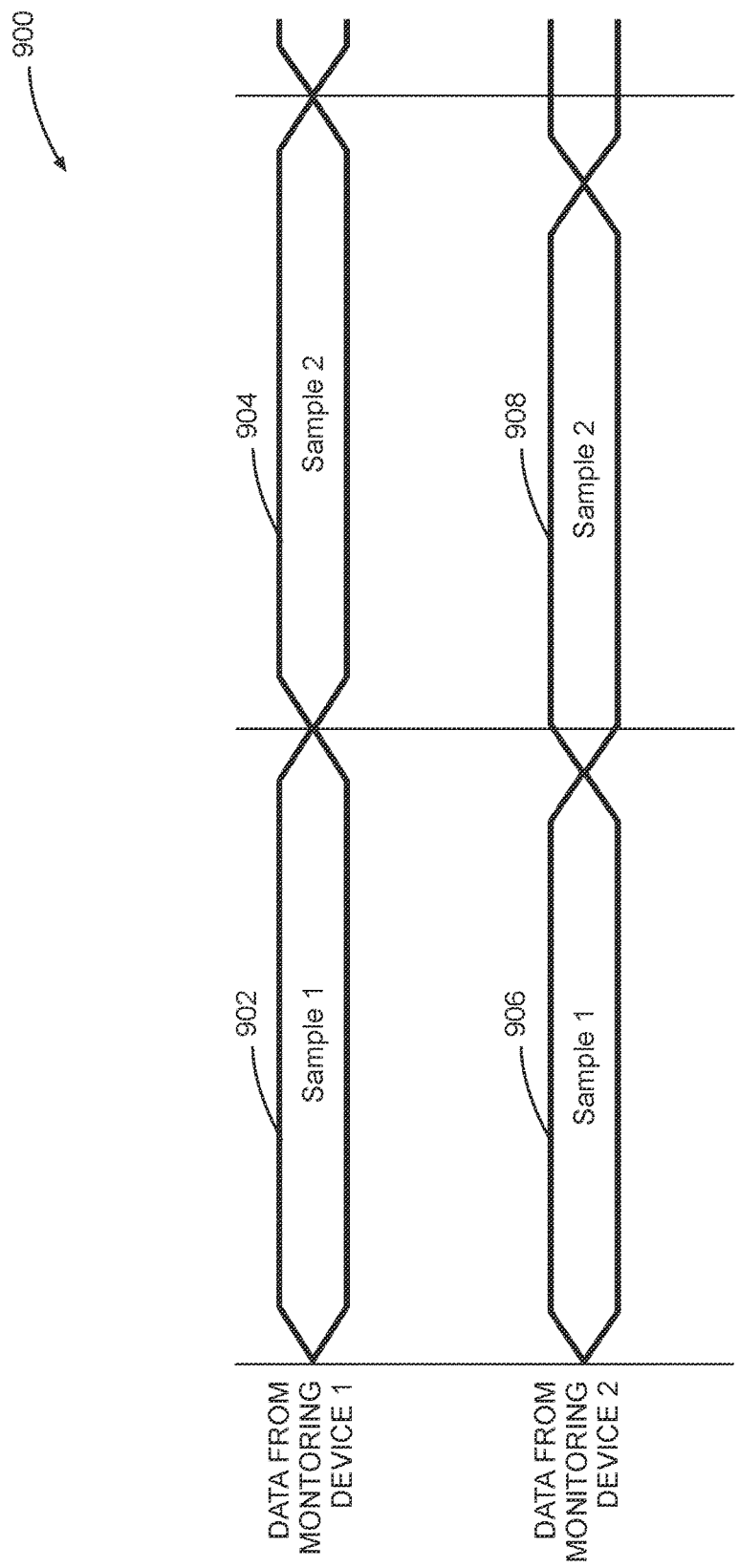
FIG. 9 is a timing diagram depicting an effect of clock bias.

FIG. 9 is a timing diagram depicting an effect 900 of clock bias. Clock bias occurs when the frequency of a clock signal deviates from a nominally specified frequency by a fixed offset. For example, for a specified clock frequency of 1 MHz, an actual frequency of a clock signal as measured may be 1.001 MHz. Over a period of time, the associated frequency deviation may result in a large time skew for a digital clocked with the 1.001 MHz clock as compared to a 1 MHz clock. This may lead to errors in constructing the biological function measurement at waveform receiver 102. Effect 900 illustrates an effect of clock bias.

Effect 900 depicts a sample 1 902 and a sample 2 904 from a monitoring device 1 (e.g., monitoring device 108), and a sample 1 906 and a sample 2 908 from a monitoring device 2 (e.g., monitoring device 110). These data samples may be data samples similar to data samples output by ADC 214. The clock signal associated with monitoring device 2 has a higher frequency as compared to the clock signal associated with monitoring device 1. Due to a shorter time interval between samples from monitoring device 2 as compared to monitoring device 1, a time skew is introduced between the waveforms. This time skew is visible in effect 900.

For each of monitoring device 108 through monitoring device 118, effects such as clock non-synchronization, clock bias and other clock effects can cause time skews between received composite chaotic waveforms from the monitoring devices. This, in turn, can cause errors in computing the associated biological measurement function by waveform receiver 102.

Figure 10:
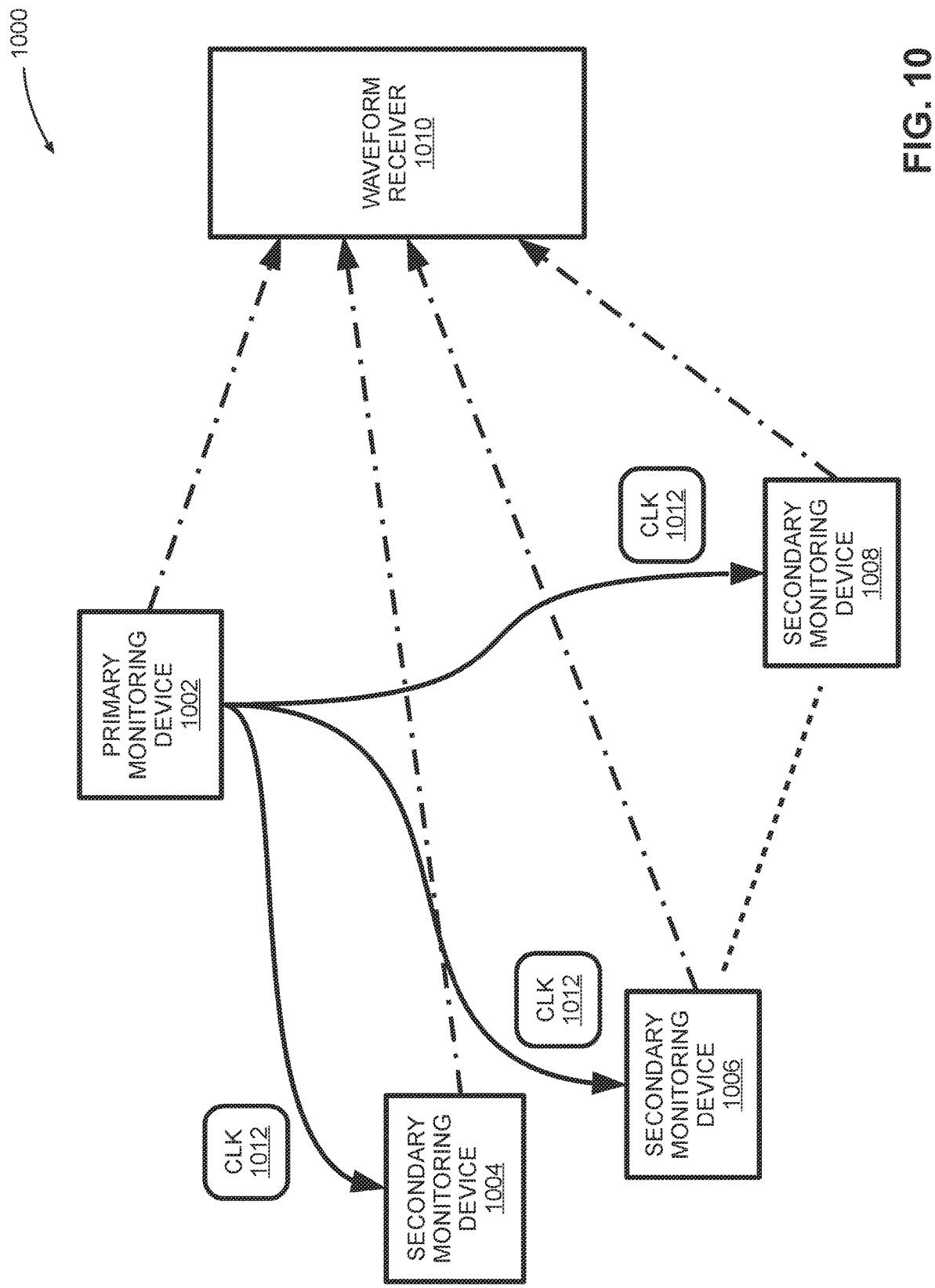
FIG. 10 is an example computer architecture of a biological measurement system that accounts for clock non-synchronization and clock bias.

FIG. 10 is an example computer architecture of a biological measurement system 1000 that accounts for clock non-synchronization and clock bias. As depicted, biological measurement system 1000 includes a waveform receiver 1010, a primary monitoring device 1002, a secondary monitoring device 1004, a secondary monitoring device 1006, through a secondary monitoring device 1008. In an aspect, each of primary monitoring device 1002 may have an architecture similar to that of monitoring device 200. Secondary monitoring device 1004 through secondary monitoring device 1008 may each have an architecture similar to that of monitoring device 200, with the only difference being that each of secondary monitoring device 1004 through secondary monitoring device 1008 does not include a clock source; instead, each of secondary monitoring device 1004 through secondary monitoring device 1008 receives a clock signal CLK 1012 from primary monitoring device 1002.

In an aspect, CLK 1012 may be generated by primary monitoring device 1002, and routed to each of secondary monitoring device 1004 through secondary monitoring device 1008. CLK 1012 may also be used as a system clock by primary monitoring device 1002. In this way, primary monitoring device 1002, and secondary monitoring device 1004 through secondary monitoring device 1008 are common-clocked and time-synchronized. Each of primary monitoring device 1002, and secondary monitoring device 1004 through secondary monitoring device 1008 transmits a composite chaotic waveform to waveform receiver 1010 for demodulation.

Figure 11:
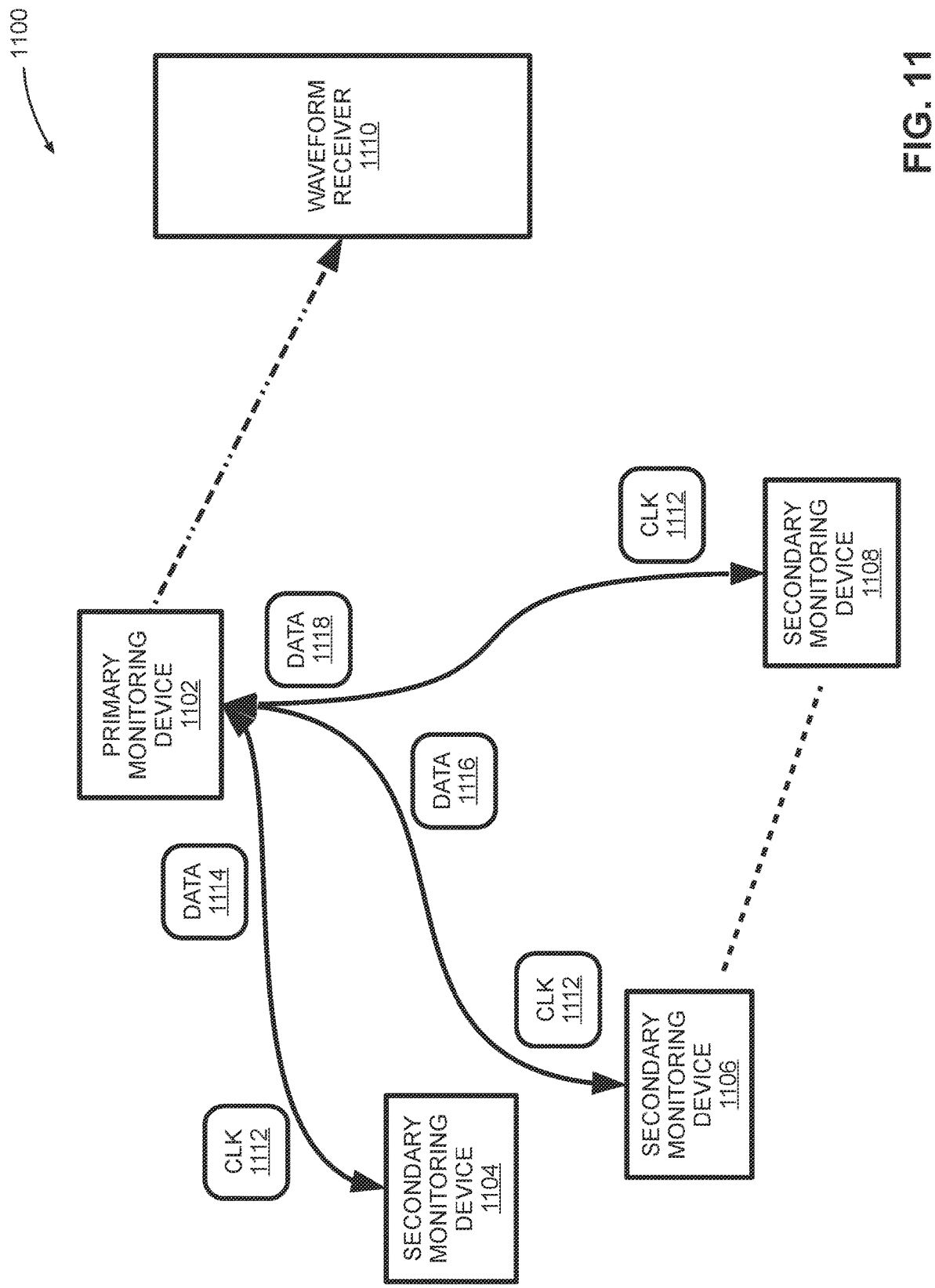
FIG. 11 is an example computer architecture of a biological measurement system that includes a clock distribution scheme.

FIG. 11 is an example computer architecture of a biological measurement system 1100 that includes a clock distribution scheme. As depicted, biological measurement system 1100 includes a waveform receiver 1110, a primary monitoring device 1102, a secondary monitoring device 1104, a secondary monitoring device 1106, through a secondary monitoring device 1108. In an aspect, each of primary monitoring device 1102 may have an architecture similar to that of monitoring device 200. Secondary monitoring device 1104 through secondary monitoring device 1108 may each have an architecture similar to that of monitoring device 200, with the only difference being that each of secondary monitoring device 1104 through secondary monitoring device 1108 does not include a clock source; instead, each of secondary monitoring device 1104 through secondary monitoring device 1108 receives a clock signal CLK 1112 from primary monitoring device 1002.

In an aspect, CLK 1112 may be generated by primary monitoring device 1102, and routed to each of secondary monitoring device 1104 through secondary monitoring device 1108. CLK 1112 may also be used as a system clock by primary monitoring device 1102. In this way, primary monitoring device 1102, and secondary monitoring device 1104 through secondary monitoring device 1108 are common-clocked and time-synchronized. Each of primary monitoring device 1102, and secondary monitoring device 1104 through secondary monitoring device 1108 transmits a composite chaotic waveform to primary monitoring device 1102 as data. For example, secondary monitoring device 1104 transmits data 1114 to primary monitoring device 1102; secondary monitoring device 1106 transmits data 1116 to primary monitoring device 1102; and so on, with secondary monitoring device 1108 transmitting data 1118 to primary monitoring device 1102. Primary monitoring device 1102 assembles all the received composite chaotic waveforms along with the composite chaotic waveform generated by primary monitoring device 1102, and transmits all the composite chaotic waveforms collectively to waveform receiver 1110 for demodulation.

Figure 12:
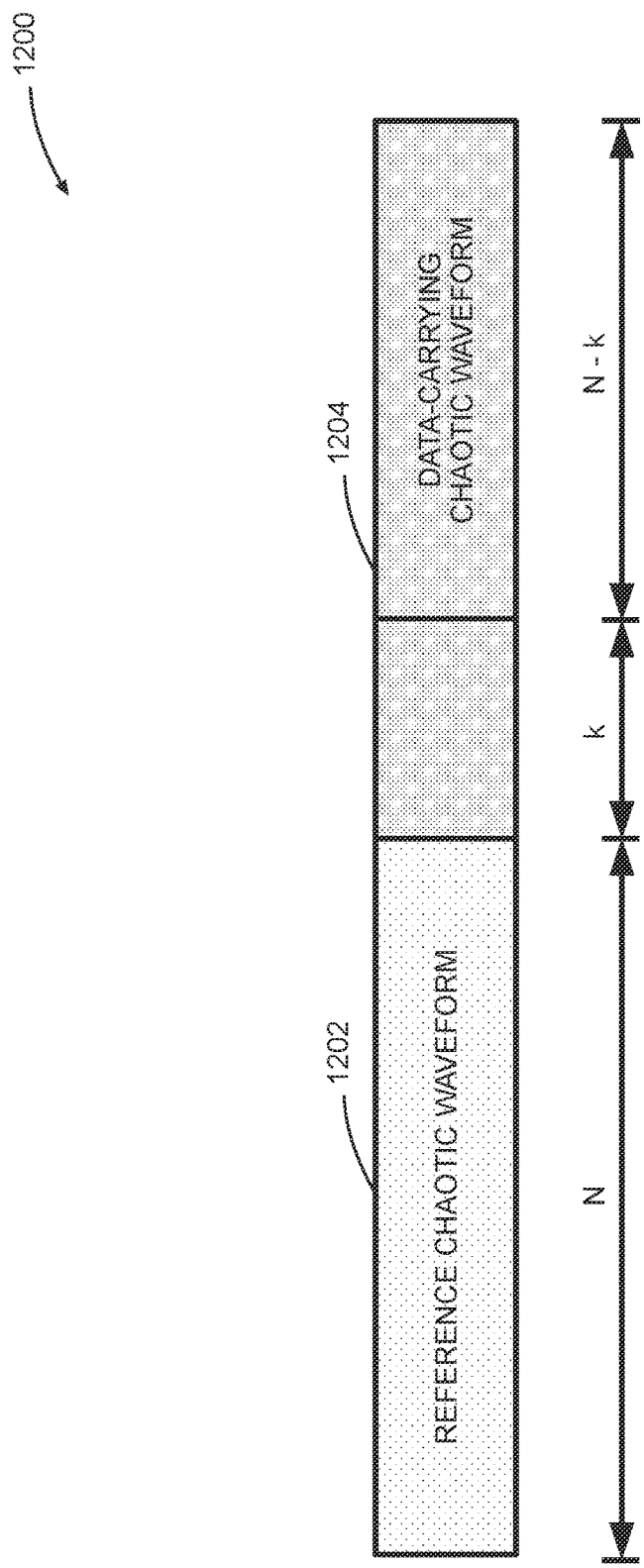
FIG. 12 is a waveform diagram depicting a composite chaotic waveform.

FIG. 12 is a waveform diagram depicting a composite chaotic waveform 1200. Composite chaotic waveform 1200 may be generated by monitoring device 200. As depicted, composite chaotic waveform 1200 includes a reference chaotic waveform 1202 of length N concatenated (i.e., combined) with an auxiliary chaotic waveform 1204 of length N. In an aspect, data received from ADC 214 may be modulated onto auxiliary chaotic waveform 1204. Specifically, auxiliary chaotic waveform 1204 may be temporally phase-shifted by k samples in accordance with a data sample received from ADC 214. For example, suppose N=1024, and suppose ADC 214 is a 10-bit ADC. If a data sample of 0 is received, then there is no phase shift (k=0). If a data sample of 1 is received, then k=1, and so on, to a data sample of 1023 corresponding to a phase shift of 1023.

At the receiver, waveform receiver 102 receives composite chaotic waveform 1200, and separately computes separate correlation functions for reference chaotic waveform 1202 and auxiliary chaotic waveform 1204. The correlation function associated with reference chaotic waveform 1202 will have a correlation peak at a time index of zero, while the correlation function associated with auxiliary chaotic waveform 1204 will have a correlation peak at a time index of k. Waveform receiver 102 compares the two correlation functions, determines the temporal difference k, and maps this difference to the associated data symbol. An advantage of this temporal phase shifting approach is that it improves a spectral efficiency associated with communication using chaotic (and other spread-spectrum) waveforms.

In an aspect, reference chaotic waveform 1202 and auxiliary chaotic waveform 1204 may be selected from an ensemble of chaotic waveforms stored in memory 224. Each of monitoring device 108 through monitoring device 118 may be associated with a unique (i.e., distinct) chaotic waveform ensemble.

Figure 13:
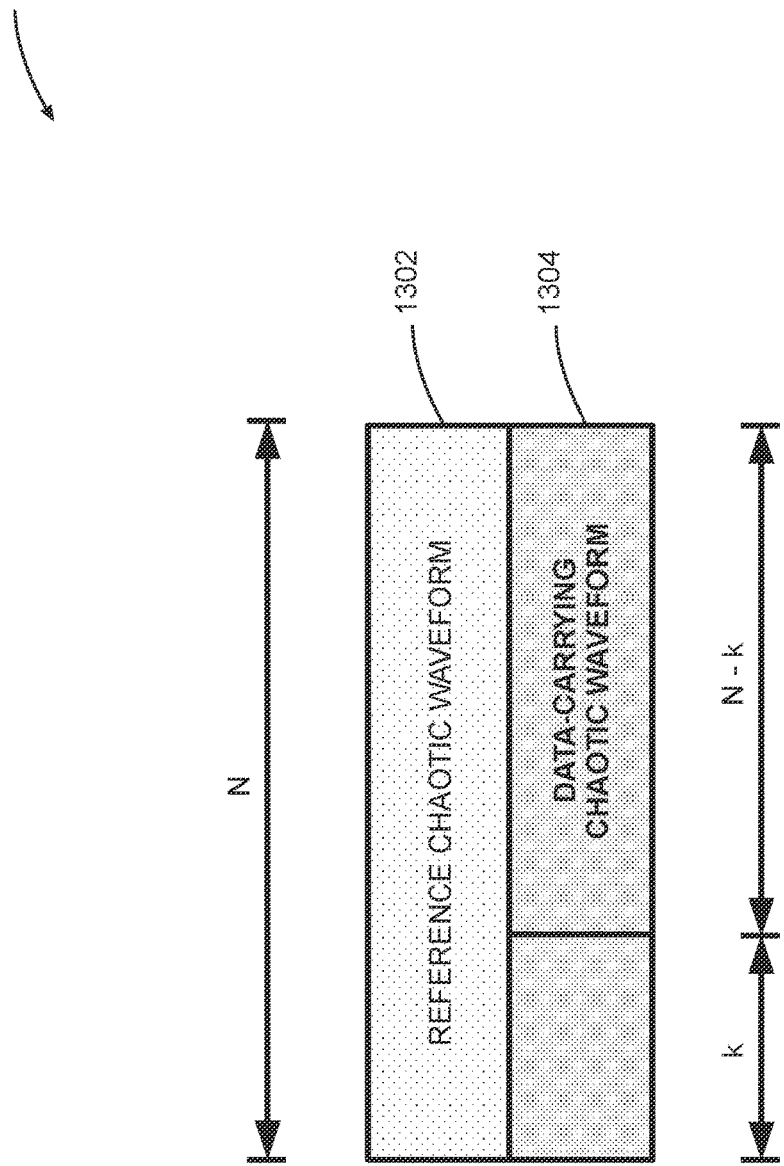
FIG. 13 is a waveform diagram depicting a composite chaotic waveform.

FIG. 13 is a waveform diagram depicting a composite chaotic waveform 1300. Composite chaotic waveform 1300 may be generated by monitoring device 200. As depicted, composite chaotic waveform 1300 includes a reference chaotic waveform 1302 of length N combined with an auxiliary chaotic waveform 1304 of length N. The combination may include a mathematical operation such as pointwise addition or multiplication. In an aspect, data received from ADC 214 may be modulated onto auxiliary chaotic waveform 1304 in a manner similar to the modulation of auxiliary chaotic waveform 1204. To construct composite chaotic waveform 1300, reference chaotic waveform 1302 may be combined with auxiliary chaotic waveform 1304 by a mathematical operation such as pointwise addition or multiplication.

In an aspect, composite chaotic waveform 1300 may be transmitted to waveform receiver 102. Waveform receiver 1302 may compute a correlation function for each of reference chaotic waveform 1302 and auxiliary chaotic waveform 1304, and perform the data demodulation process in a manner similar to that described for composite chaotic waveform 1200.

In an aspect, reference chaotic waveform 1302 and auxiliary chaotic waveform 1304 may be selected from an ensemble of chaotic waveforms stored in memory 224. Each of monitoring device 108 through monitoring device 118 may be associated with a unique (i.e., distinct) chaotic waveform ensemble.

Figure 14:
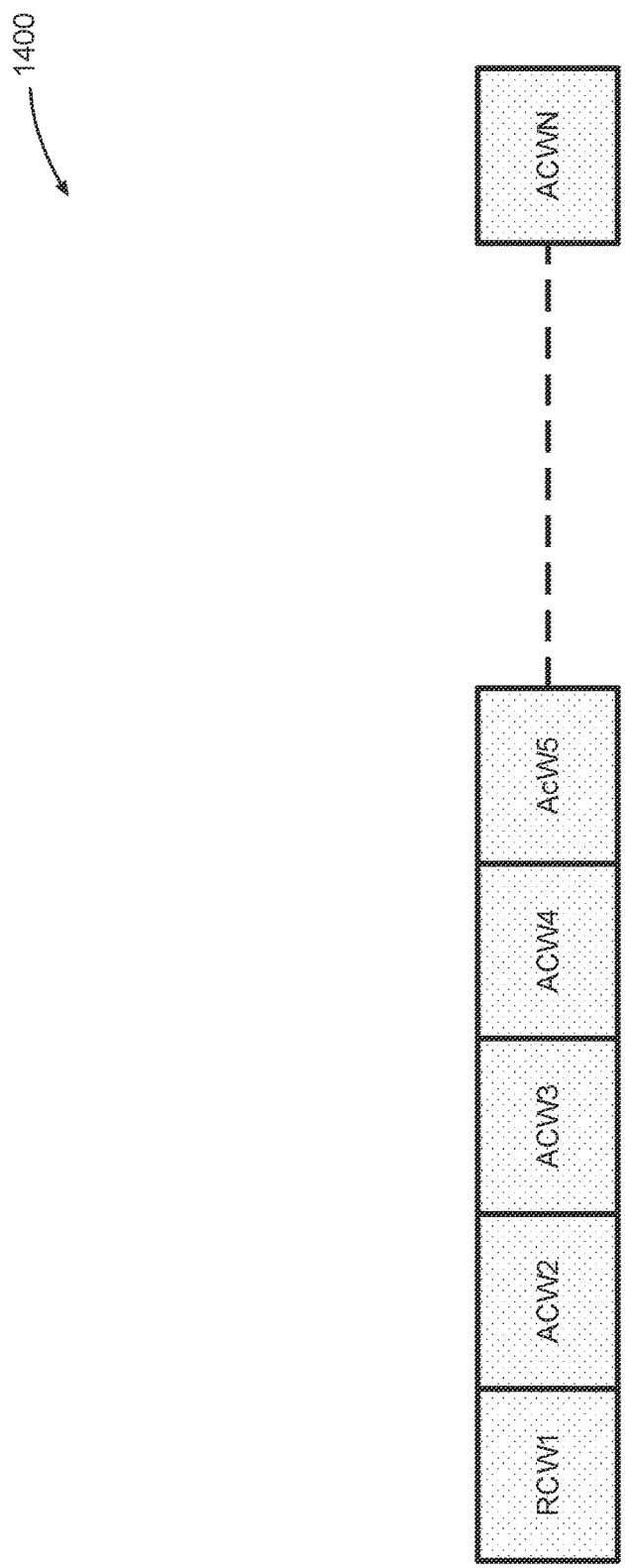
FIG. 14 is a waveform diagram depicting a composite chaotic waveform.

FIG. 14 is a waveform diagram depicting a composite chaotic waveform 1400. As depicted, composite chaotic waveform 1400 is comprised of a reference chaotic waveform RCW1, concatenated with an auxiliary chaotic waveform ACW2, an auxiliary chaotic waveform ACW3, an auxiliary chaotic waveform ACW4, an auxiliary chaotic waveform ACW5, through an auxiliary chaotic waveform ACWN. Each of ACW2 through ACWN may be independently modulated by distinct data samples received from ADC 214, using the temporal phase shifting process described for auxiliary chaotic waveform 1204. Composite chaotic waveform 1400 may be demodulated at waveform receiver 102 using independent correlation functions for each of RCW1, and ACW2 through ACWN. A correlation peak associated with a correlation function for each of ACW2 through ACWN is compared with the correlation peak associated with a correlation function for RCW1, and the corresponding phase shifts are appropriately mapped to demodulated data symbols. In an aspect, RCW1, and ACW2 thorough ACWN may be selected from an ensemble of chaotic waveforms stored in memory 224. Each of monitoring device 108 through monitoring device 118 may be associated with a unique (i.e., distinct) chaotic waveform ensemble.

Figure 15:
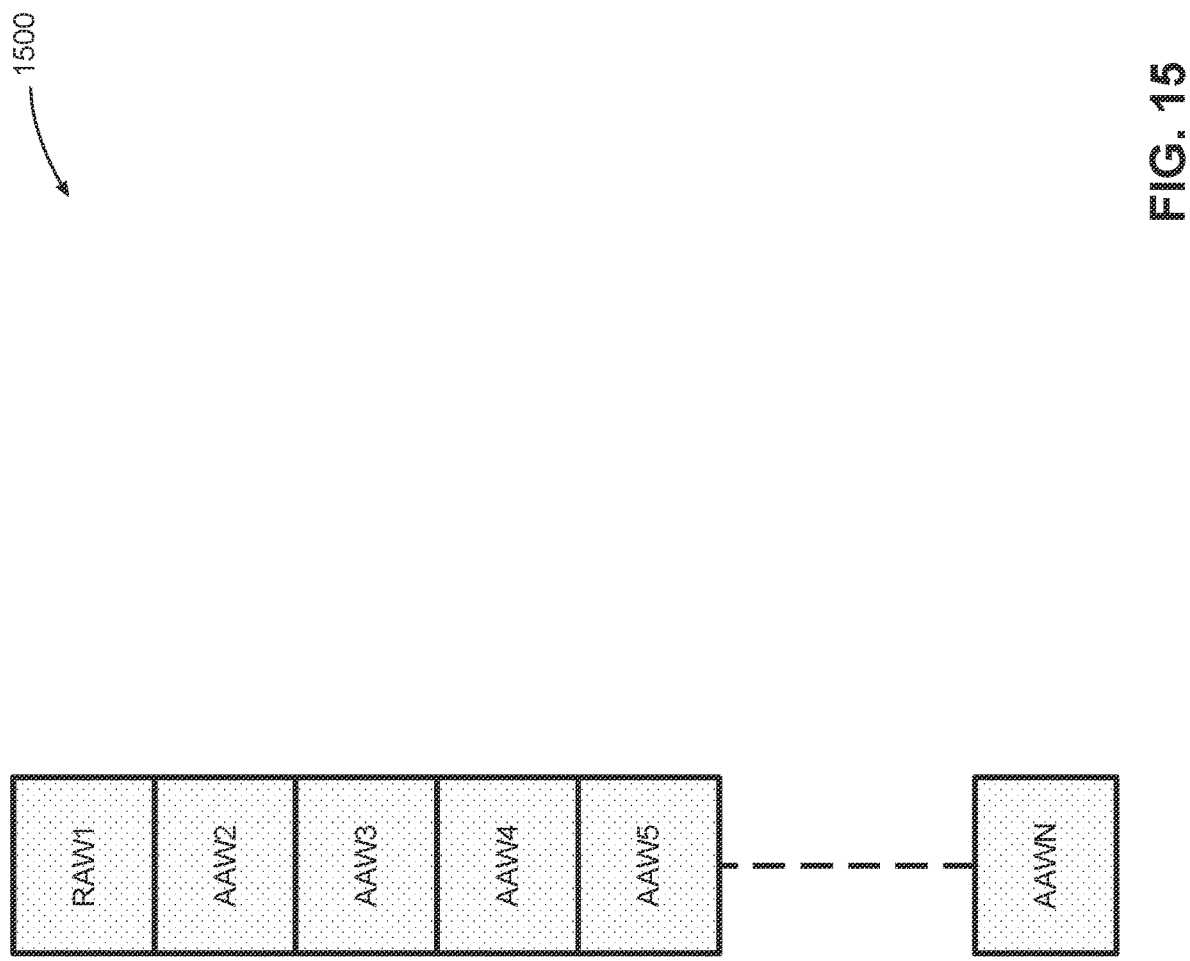
FIG. 15 is a waveform diagram depicting a composite chaotic waveform.

FIG. 15 is a waveform diagram depicting a composite chaotic waveform 1500. As depicted, composite chaotic waveform 1500 is comprised of a reference chaotic waveform RAW1, combined with an auxiliary chaotic waveform AAW2, an auxiliary chaotic waveform AAW3, an auxiliary chaotic waveform AAW4, an auxiliary chaotic waveform AAW5, through an auxiliary chaotic waveform AAWN, via pointwise addition or multiplication. Each of AACW2 through AAWN may be independently modulated by distinct data samples received from ADC 214, using the temporal phase shifting process described for auxiliary chaotic waveform 1204. Composite chaotic waveform 1500 may be demodulated at waveform receiver 102 using independent correlation functions for each of RAW1, and AAW2 through AAWN. A correlation peak associated with a correlation function for each of AAW2 through AAWN is compared with the correlation peak associated with a correlation function for RAW1, and the corresponding phase shifts are appropriately mapped to demodulated data symbols. In an aspect, RAW1, and AAW2 thorough AAWN may be selected from an ensemble of chaotic waveforms stored in memory 224. Each of monitoring device 108 through monitoring device 118 may be associated with a unique (i.e., distinct) chaotic waveform ensemble.

A direct application of biological measurement system 100 is an ECG/EKG monitoring system. An example system may include six monitoring devices attached at different points on a human body. A typical bandwidth required for ECG/EKG data is 125 Hz. This relates to a 250 sps sample rate by ADC 214. Assuming 10-bit A/D conversion by ADC 214, this translates to a 2.5 kbps required transmission data bitrate for each monitoring device. To achieve this, a N=1024 may be chosen for the chaotic waveform length. Each monitoring device may generate a composite chaotic waveform is constructed in a manner similar to composite chaotic waveform 1500. In an aspect, all monitoring devices may be common-clocked (e.g., biological measurement system 1000), and may sleep for a time period corresponding to 1024 samples between transmissions.

The chaotic waveforms may be clocked at a 300 kHz data rate. The selected sample rate for ADC 214 may be defined as 2*300,000/2048=292.97 Hz. This is greater than the required sample rate for ADC 214. In other words, within a single composite chaotic waveform transmission period, ADC 214 produces 2 ECG/EKG samples per monitoring device. These two 10-bit data samples are each modulated onto a distinct 1024-point auxiliary chaotic waveform. These two modulated auxiliary chaotic waveforms are combined with (e.g., added to) a 1024-point reference chaotic waveform, and transmitted to waveform receiver 102. This is done for each monitoring device. Waveform receiver 102 receives and demodulates the received composite chaotic waveforms, performs the requisite ECG/EKG processing, and outputs an ECG waveform onto a suitable display device.

Another aspect to consider for an ECG application is common-mode noise rejection. Contemporary wired ECG systems oftentimes use a leg drive circuit, where a portion of the ECG measurements are fed back to the patient's body via a transducer to reduce noise. With a wireless system, using any kind of feedback system will involve designing a full chaotic receiver in a monitoring system. This will make the monitoring system inefficient on power, and large and heavy due to the computing resources required. Alternatives to leg drive circuitry for common mode noise rejection include digital post processing methods such as digital filtering (e.g., FIR filtering). Since ECG data is digitized directly at the source rather than being processed collectively by analog circuitry, all processing needs to be performed in the digital domain by waveform receiver (specifically, data processor 520) for wireless transducer applications.

Figure 16:
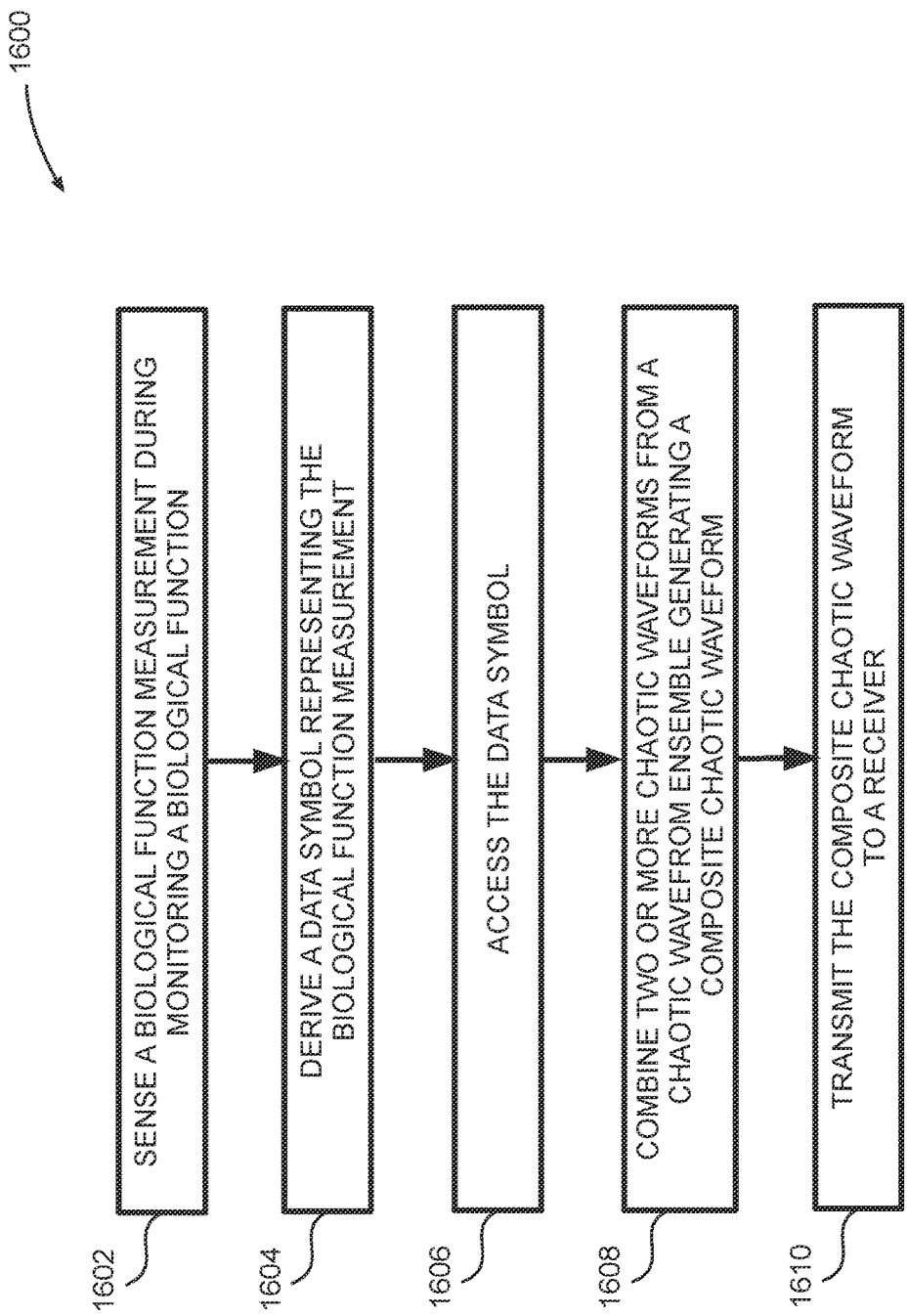
FIG. 16 is a flow diagram depicting a method to generate a composite chaotic waveform.

FIG. 16 is a flow diagram depicting a method 1600 to generate a composite chaotic waveform. Referring briefly and concurrently back to FIG. 2, method 1600 will be described with respect to the components of monitoring device 200. Method 1600 includes sensing a biological function measurement monitoring a biological function (1602). For example, sensor 212 may sense an ECG/EKG signal while monitoring an ECG/EKG function.

Method 1600 includes deriving a data symbol representing the biological function measurement (1604). For example, ADC 214 may derive a digital data symbol by converting an analog signal sensed by sensor 212.

Method 1600 includes accessing the data symbol (1606). For example, processor 216 may access (i.e., read in or receive) the digital data symbol from ADC 214.

Method 1600 includes combining two or more chaotic waveforms from a chaotic waveform ensemble generating a composite chaotic waveform (1608). For example, processor 216 may combine two or more chaotic waveforms from a chaotic waveform ensemble stored in memory 224 to generate a composite chaotic waveform (e.g., composite chaotic waveform 1500). In an aspect, a combination of chaotic waveforms is used to represent the digital data symbol in a composite chaotic waveform that may take the form of composite chaotic waveform 1300, composite chaotic waveform 1400, composite chaotic waveform 1500, or any other composite chaotic waveform.

Method 1600 includes transmitting the composite chaotic waveform to a receiver (1610). For example, the composite chaotic waveform may be transmitted by 216 to DAC 218, by DAC 218 to RFFE 202, by RFFE 202 to transmit antenna 210, and then to waveform receiver 102.

Figure 17A:
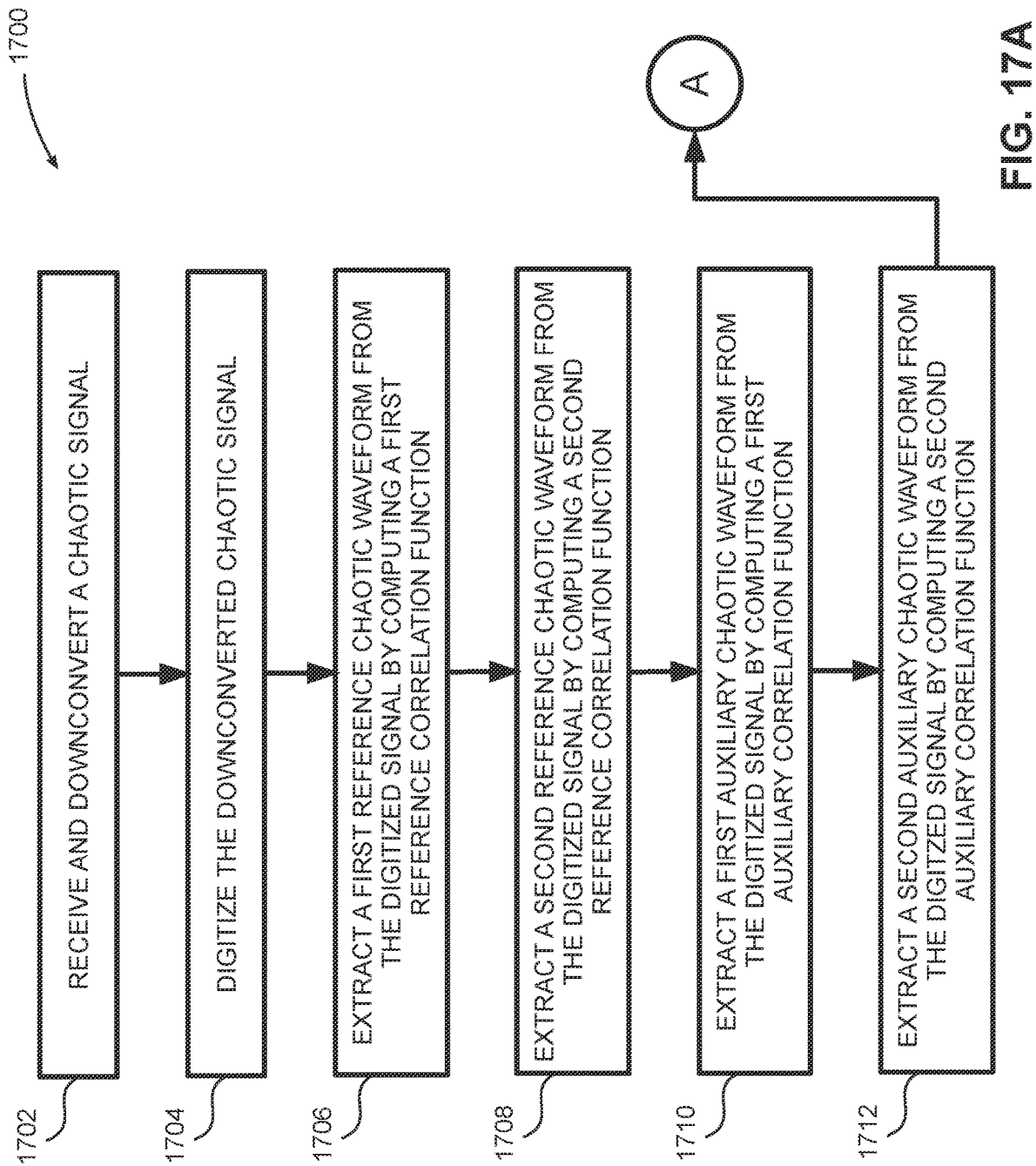

FIG. 17A is a flow diagram depicting a method 1700 to compute a biological function measurement. Referring briefly and concurrently back to FIG. 5, method 1700 will be described with respect to the components of waveform receiver 500. Method 1700 may include receiving and downconverting a chaotic signal (1702). In an aspect, the chaotic signal may be comprised of multiple composite chaotic waveforms, with each composite chaotic waveform being transmitted by a monitoring device (e.g., monitoring device 108). The chaotic signal may be received by receive antenna 510 and downconverted by RFFE 512. Method 1700 may include digitizing the downconverted chaotic signal (1704). In an aspect, the digitizing may be performed by ADC 514.

Method 1700 may include extracting a first reference chaotic waveform from the digitized signal by computing a first reference correlation function (1706). For example, chaotic demodulator 512 may be configured to perform a correlation on the digitized signal. The correlation may use a locally-stored copy of a first reference chaotic waveform that enables chaotic demodulator 512 to extract the first reference chaotic waveform from the digitized signal by computing a first reference correlation function. For example, the first reference chaotic waveform may be a part of a composite chaotic waveform transmitted by monitoring device 108.

Method 1700 may include extracting a second reference chaotic waveform from the digitized signal by computing a second reference correlation function (1708). For example, chaotic demodulator 512 may be configured to perform a correlation on the digitized signal. The correlation may use a locally-stored copy of a second reference chaotic waveform that enables chaotic demodulator 512 to extract the second reference chaotic waveform from the digitized signal by computing a second reference correlation function. For example, the second reference chaotic waveform may be a part of a composite chaotic waveform transmitted by monitoring device 110.

Method 1700 may include extracting a first auxiliary chaotic waveform from the digitized signal by computing a first auxiliary correlation function (1710). For example, chaotic demodulator 512 may be configured to perform a correlation on the digitized signal. The correlation may use a locally-stored copy of a first auxiliary chaotic waveform that enables chaotic demodulator 512 to extract the first auxiliary chaotic waveform from the digitized signal by computing a first auxiliary correlation function. For example, the first auxiliary chaotic waveform may be a part of a composite chaotic waveform transmitted by monitoring device 108.

Method 1700 may include extracting a second auxiliary chaotic waveform from the digitized signal by computing a second auxiliary correlation function (1712). For example, chaotic demodulator 512 may be configured to perform a correlation on the digitized signal. The correlation may use a locally-stored copy of a second auxiliary chaotic waveform that enables chaotic demodulator 512 to extract the second auxiliary chaotic waveform from the digitized signal by computing a second auxiliary correlation function. For example, the second auxiliary chaotic waveform may be a part of a composite chaotic waveform transmitted by monitoring device 110.

Method 1700 then goes to A, with a continued description provided in the description of FIG. 17B.

FIG. 17B is a flow diagram depicting a continuation of method 1700. Starting from A, method 1700 may include performing a first comparison between the first reference correlation function and the first auxiliary correlation function (1714). For example, chaotic demodulator 512 may perform a first comparison between the first reference correlation function and the first auxiliary correlation function.

Method 1700 may include extracting a first data symbol from the first comparison, the first data symbol being associated with a biological function measurement (1716). For example, chaotic demodulator 512 may extract a first data symbol from the first comparison.

Method 1700 may include performing a second comparison between the second reference correlation function and the second auxiliary correlation function (1718). For example, chaotic demodulator 512 may perform a second comparison between the second reference correlation function and the second auxiliary correlation function.

Method 1700 may include extracting a second data symbol from the second comparison, the second data symbol being associated with the biological function measurement (1720). For example, chaotic demodulator 512 may extract a second data symbol from the second comparison.

Method 1700 may include processing the first data symbol and the second data symbol (1722). For example, data processor 520 may process the first data symbol and the second data symbol.

Method 1700 may include computing the biological function measurement responsive to the processing (1722). For example, data processor 520 may compute the biological function measurement (e.g., an ECG/EKG measurement) responsive to processing the first data symbol and the second data symbol.

Although the present disclosure is described in terms of certain example embodiments, other embodiments will be apparent to those of ordinary skill in the art, given the benefit of this disclosure, including embodiments that do not provide all of the benefits and features set forth herein, which are also within the scope of this disclosure. It is to be understood that other embodiments may be utilized, without departing from the scope of the present disclosure.

What is claimed is:

1. A biological function monitoring system, comprising:
a first monitoring device, including a first sensor, a first processor, and a first transmitter, and wherein:
the first sensor is configured to:
sense a first biological function measurement during monitoring a biological function; and
derive a first data symbol representing the first biological function measurement;
the first processor is configured to:
access the first data symbol from the first sensor; and
combine two or more chaotic waveforms from a first chaotic waveform ensemble generating a first composite chaotic waveform representative of the first data symbol; and
the first transmitter is configured to transmit the first composite chaotic waveform to a receiver over a communication channel;
a second monitoring device, including a second sensor, a second processor, and a second transmitter, and wherein:
the second sensor is configured to:
sense a second biological function measurement during the monitoring of the biological function; and
derive a second data symbol representing the second biological function measurement;
the second processor is configured to:
access the second data symbol from the second sensor; and
combine two or more chaotic waveforms from a second chaotic waveform ensemble, distinct from the first chaotic waveform ensemble, generating a second composite chaotic waveform representative of the second data symbol;
the second transmitter configured to transmit the second composite chaotic waveform to the receiver over the communication channel; and
clock distribution circuitry configured to route a common clock signal between the first monitoring device and the second monitoring device such that the first composite chaotic waveform and the second composite chaotic waveform are substantially synchronized at a digital sample level.

2. The biological function monitoring system of claim 1, wherein the first processor is further configured to:
select a first chaotic waveform from the first chaotic waveform ensemble, the first chaotic waveform representing a reference waveform;
select a second chaotic waveform from the first chaotic waveform ensemble, the second chaotic waveform representing a data-carrying waveform; and
temporally phase-shifting the second chaotic waveform with respect to the first chaotic waveform in accordance with the first data symbol.

3. The biological function monitoring system of claim 1, wherein the first sensor is a biomedical transducer.

4. The biological function monitoring system of claim 3, wherein the biomedical transducer is an electrocardiogram (ECG) transducer.

5. The biological function monitoring system of claim 1, wherein the communication channel is a wireless communication channel.

6. The biological function monitoring system of claim 1, further comprising the first processor generating the first chaotic waveform ensemble.

7. The biological function monitoring system of claim 1, further comprising a memory associated with the first monitoring device, the memory configured to store the first chaotic waveform ensemble.

8. The biological function monitoring system of claim 1, wherein the first processor is any of a digital signal processor (DSP), a field-programmable gate array (FPGA), a microcontroller, or a customized integrated circuit processor.

9. A method comprising:
receiving a first composite chaotic waveform, the first composite chaotic waveform being comprised of at least two distinct chaotic waveforms from a first chaotic waveform ensemble, the first composite chaotic waveform representing a first data symbol associated with a biological function measurement;
receiving a second composite chaotic waveform substantially time-synchronized with the first composite chaotic waveform at a digital sample level, the second composite chaotic waveform being comprised of at least two distinct chaotic waveforms from a second chaotic waveform ensemble distinct from the first chaotic waveform ensemble, the second composite chaotic waveform representing a second data symbol associated with the biological function measurement;
performing a first demodulation on the at least two distinct chaotic waveforms from the first composite chaotic waveform;
deriving a first biological signal responsive to the first demodulation;
performing a second demodulation on the at least two distinct chaotic waveforms from the second composite chaotic waveform;
deriving a second data symbol responsive to the second demodulation;
processing the first data symbol and the second data symbol; and
computing the biological function measurement responsive to the processing.

10. The method of claim 9, wherein the biological function measurement is an electrocardiogram (ECG) measurement.

11. The method of claim 9, wherein the first demodulation comprises:
performing a first correlation of the first composite chaotic waveform with a reference chaotic waveform to determine a first correlation function;
performing a second correlation of the first composite chaotic waveform with an auxiliary chaotic waveform to determine a second correlation function;
determining a phase shift between the first correlation function and the second correlation function; and
mapping the phase shift to the first data symbol.

12. The method of claim 9, wherein the first composite chaotic waveform and the second composite chaotic waveform are received over a wireless communication channel.

13. A chaotic communication receiver comprising:
a radio frequency (RF) front end configured to wirelessly receive a chaotic signal and downconvert the chaotic signal, wherein the received chaotic signal is comprised of a first composite chaotic waveform further comprising a first reference chaotic waveform and a first auxiliary chaotic waveform, and a second composite chaotic waveform further comprising a second reference chaotic waveform and a second auxiliary chaotic waveform, wherein the first composite chaotic waveform and the second reference chaotic waveform are substantially time-synchronized at a digital sample level;

a mixed-signal device configured to digitize the down-converted chaotic signal; and a chaotic demodulator configured to:

extract the first reference chaotic waveform from the digitized chaotic signal by computing a first reference correlation function;

extract the second reference chaotic waveform from the digitized chaotic signal by computing a second reference correlation function;

extract the first auxiliary chaotic waveform from the digitized chaotic signal by computing a first auxiliary correlation function;

extract the second auxiliary chaotic waveform from the digitized chaotic signal by computing a second auxiliary correlation function;

perform a first comparison between the first reference correlation function and the first auxiliary correlation function;

extract a first data symbol from the first comparison, the first data symbol being associated with a biological function measurement;

perform a second comparison between the second reference correlation function and the second auxiliary correlation function;

extract a second data symbol from the second comparison, the second data symbol being associated with the biological function measurement;

process the first data symbol and the second data symbol; and compute the biological function measurement responsive to the processing.

14. The chaotic communication receiver of claim 13, wherein the chaotic demodulator includes a plurality of processing cores.

15. The chaotic communication receiver of claim 14, wherein each of the first reference correlation function, the second reference correlation function, the first auxiliary correlation function, and the second auxiliary correlation function is computed in a distinct processing core.

16. The chaotic communication receiver of claim 14, wherein each of the first comparison and the second comparison is performed in a distinct processing core.

17. The chaotic communication receiver of claim 13, wherein the chaotic demodulator further includes a carrier tracking loop and a code tracking loop for coherent demodulation of the first reference chaotic waveform.

18. The chaotic communication receiver of claim 13, wherein the biological function measurement is an electrocardiogram (ECG).

19. The chaotic communication receiver of claim 13, wherein the chaotic demodulator is implemented using any of a digital signal processor (DSP), a field-programmable gate array (FPGA), a microcontroller, or a customized integrated circuit processor.

20. The chaotic communication receiver of claim 13, wherein the chaotic demodulator includes a graphics processing unit (GPU) array.

* * * * *